US009765345B2

(12) United States Patent
Ochiai et al.

(10) Patent No.: US 9,765,345 B2
(45) Date of Patent: Sep. 19, 2017

(54) **PROMOTER EXHIBITING HIGH EXPRESSION ACTIVITY IN *MORTIERELLA* MICROORGANISMS**

(71) Applicant: SUNTORY HOLDINGS LIMITED, Osaka (JP)

(72) Inventors: Misa Ochiai, Osaka (JP); Jun Ogawa, Kyoto (JP); Eiji Sakuradani, Kyoto (JP); Akinori Ando, Kyoto (JP)

(73) Assignee: SUNTORY HOLDINGS LIMITED, Osaka (JP)

( * ) Notice: Subject to any disclaimer, the term of this patent is extended or adjusted under 35 U.S.C. 154(b) by 0 days.

(21) Appl. No.: 14/779,080

(22) PCT Filed: Mar. 26, 2014

(86) PCT No.: PCT/JP2014/059698
§ 371 (c)(1),
(2) Date: Sep. 22, 2015

(87) PCT Pub. No.: WO2014/157736
PCT Pub. Date: Oct. 2, 2014

(65) Prior Publication Data
US 2016/0152992 A1    Jun. 2, 2016

(30) Foreign Application Priority Data
Mar. 27, 2013  (JP) ................................ 2013-066265

(51) Int. Cl.
*C12N 15/00* (2006.01)
*C12N 15/80* (2006.01)
*C07K 14/37* (2006.01)

(52) U.S. Cl.
CPC .............. *C12N 15/80* (2013.01); *C07K 14/37* (2013.01)

(58) Field of Classification Search
CPC ........................ C12N 15/8216; C07K 14/415
USPC ....................................................... 536/24.1
See application file for complete search history.

(56) References Cited

U.S. PATENT DOCUMENTS

2010/0203218 A1    8/2010  Ochiai et al.

FOREIGN PATENT DOCUMENTS

| CA | 1340433 | 3/1999 |
| EP | 2169055 A1 | 3/2010 |
| JP | 63-044891 A | 2/1988 |

OTHER PUBLICATIONS

Mackenzie et al., "Isolation and Use of a Homologous Histone H4 Promoter and a Ribosomal DNA Region in a Transformation Vector for the Oil-Producing Fungus *Mortierella alpina*," Applied and Environmental Microbiology, vol. 66, No. 11, pp. 4655-4661, 2000.
Blazeck et al., "Tuning Gene Expression in *Yarrowia lipolytica* by a Hybrid Promoter Approach," Applied and Environmental Microbiology, vol. 77, No. 22, pp. 7905-7914, 2011.
Okuda et al., "Selection and Characterization of Promoters Based on Genomic Approach for the Molecular Breeding of Oleaginous Fungus *Mortierella alpina* 1S-4," Curr. Genet., published online Feb. 22, 2014 (9 pages).
Müller et al., "Comparison of Expression Systems in the Yeasts *Saccharomyces cerevisiae*, *Hansenula polymorpha*, *Klyveromyces lactis*, *Schizosaccharomyces pombe* and *Yarrowia lipolytica*. Cloning of Two Novel Promoters from *Yarrowia lipolytica*", Yeast 14, pp. 1267-1283, 1998.
Amarasinghe et al., "Genomic Approaches to the Discovery of Promoters for Sustained Expression in Cotton (*Gossypium hirsutum* L.) under Field Conditions: Expression Analysis in Transgenic Cotton and Arabidopsis of a Rubisco Small Subunit Promoter Identified using EST Sequence Analysis and cDNA Microarrays," Plant Biotechnology 23, pp. 437-450, 2006.
Okuda et al., "Characterization of galactose-dependent promoters from an oleaginous fungus *Mortierella alpina* 1S-4," Curr. Genet., vol. 60, pp. 175-182, 2014.
Park et al., "Galactose-inducible expression systems in *Candida maltosa* using promoters of newly-isolated *GAL1* and *GAL10* genes," Yeast, vol. 13, pp. 21-29, 1997.
Seiboth et al., "The *Hypocrea jecorina gal10* (uridine 5'-diphosphate-glucose 4-epimerase-encoding) gene differs from yeast homologues in structure, genomic organization, and expression" Gene, vol. 295, pp. 143-149, 2002.
Extended European Search Report issued in EP Patent App. 14776138.1, dated Nov. 14, 2016.
International Search Report issued in PCT/JP2014/059698, dated Jul. 1, 2014, along with an English language translation.

*Primary Examiner* — Tekchand Saidha
(74) *Attorney, Agent, or Firm* — Greenblum & Bernstein, P.L.C.

(57) ABSTRACT

The present invention aims to provide a promoter showing high expression activity in microorganisms belonging to the genus *Mortierella*. The present invention provides a polynucleotide which contains a nucleotide sequence selected from SEQ ID NOs: 1 to 28, or a variant thereof, as well as a non-human transformant containing such a polynucleotide.

7 Claims, 13 Drawing Sheets

Figure 12B

PROMOTER EXHIBITING HIGH EXPRESSION ACTIVITY IN *MORTIERELLA* MICROORGANISMS

The instant application contains a Sequence Listing which has been submitted electronically in ACSII format and is hereby incorporated by reference in its entirety. Said ACSII copy, created on Jan. 15, 2016, is named P48418_SL.txt and is 83,218 bytes in size.

TECHNICAL FIELD

The present invention provides a promoter showing high expression activity in cells of microorganisms belonging to the genus *Mortierella*, a vector comprising such a promoter, a non-human transformant transformed with such a promoter, as well as a method for production of proteins, lipids or fatty acids using such a promoter or transformant.

BACKGROUND ART

Techniques to produce useful compounds through microbial metabolism (fermentation techniques in a broad sense) have been developed and used practically. For example, fungi of the genus *Mortierella* (e.g., *Mortierella alpina*) are known to produce polyunsaturated fatty acids (PUFAs) including arachidonic acid and are fungi particularly useful for industrial purposes (Patent Document 1).

For use of these fungi, breeding has been conducted, i.e., modifications have been made to improve the genetic traits of useful organisms (variety improvement). Particularly in fermentation techniques, breeding becomes very important in terms of improving the efficiency of microbial production of useful compounds and reducing the production costs of these compounds, etc.

To breed useful organisms having more desirable traits, transformation-based techniques are used. In this case, a DNA fragment encoding a protein necessary to acquire a desired trait is made expressible under the control of an appropriate gene promoter and then introduced into a useful organism to be bred (i.e., a host) to obtain a population of transformants. From among this population, a desired variety (strain) will then be selected. This procedure requires a gene promoter which is appropriate for the type of organism serving as a host or appropriate for the trait to be modified.

As to the transformation of filamentous fungi to which fungi of the genus *Mortierella* belong, many techniques have been reported. Moreover, in relation to the lipid production ability of fungi of the genus *Mortierella*, many enzyme genes involved in lipid synthesis systems have been obtained. However, there have been few reports about gene promoters required to introduce these useful enzyme genes into fungi of the genus *Mortierella* and to cause their expression at high levels.

PATENT DOCUMENTS

Patent Document 1: JP 63-044891 A

DISCLOSURE OF THE INVENTION

Under these circumstances, there is a demand for the breeding of strains which produce useful lipids efficiently. For this purpose, gene promoters suitable for fungi of the genus *Mortierella* are required.

As a result of extensive and intensive efforts, the inventors of the present invention have succeeded in cloning a promoter for a gene highly expressed in *Mortierella alpina* (*M. alpina*), and thereby have completed the present invention. Namely, the present invention provides a polynucleotide, an expression vector, a transformant, and a method for production of proteins, lipids or fatty acids using such a polynucleotide or transformant, as shown below.

In more detail, the present invention is as follows.

[1] A polynucleotide of any one selected from the group consisting of (a) to (c) shown below:
(a) a polynucleotide which contains any one nucleotide sequence selected from the group consisting of SEQ ID NOs: 1 to 28;
(b) a polynucleotide which has a nucleotide sequence sharing an identity of 90% or more with any one nucleotide sequence selected from the group consisting of SEQ ID NOs: 1 to 28 and which shows promoter activity in cells of microorganisms belonging to the genus *Mortierella*; and
(c) a polynucleotide which is hybridizable under stringent conditions with a polynucleotide consisting of a nucleotide sequence complementary to any one nucleotide sequence selected from the group consisting of SEQ ID NOs: 1 to 28 and which shows promoter activity in cells of microorganisms belonging to the genus *Mortierella*.

[2] The polynucleotide according to [1] above, wherein the promoter activity is confirmed as GUS protein activity of at least 500 nmol/(mg·min) upon expression of GUS reporter gene in cells of microorganisms belonging to the genus *Mortierella*.

[3] The polynucleotide according to [1] above, which contains any one nucleotide sequence selected from the group consisting of SEQ ID NOs: 1 to 28.

[4] The polynucleotide according to [1] or [2] above, which is DNA.

[5] A vector containing the polynucleotide according to any one of [1] to [4] above.

[6] A non-human transformant transformed with the polynucleotide according to any one of [1] to [4] above.

[7] A non-human transformant transformed with the vector according to [6] above.

[8] The transformant according to [7] or [8] above, wherein the transformant is a lipid-producing fungus.

[9] The transformant according to [8] above, wherein the lipid-producing fungus is *Mortierella alpina*.

When used as a promoter, the polynucleotide of the present invention allows highly efficient expression of a target gene in cells of microorganisms belonging to the genus *Mortierella*.

BRIEF DESCRIPTION OF THE DRAWINGS

FIG. 12B is continued from FIG. 12A.

BEST MODES FOR CARRYING OUT THE INVENTION

Figure 1:
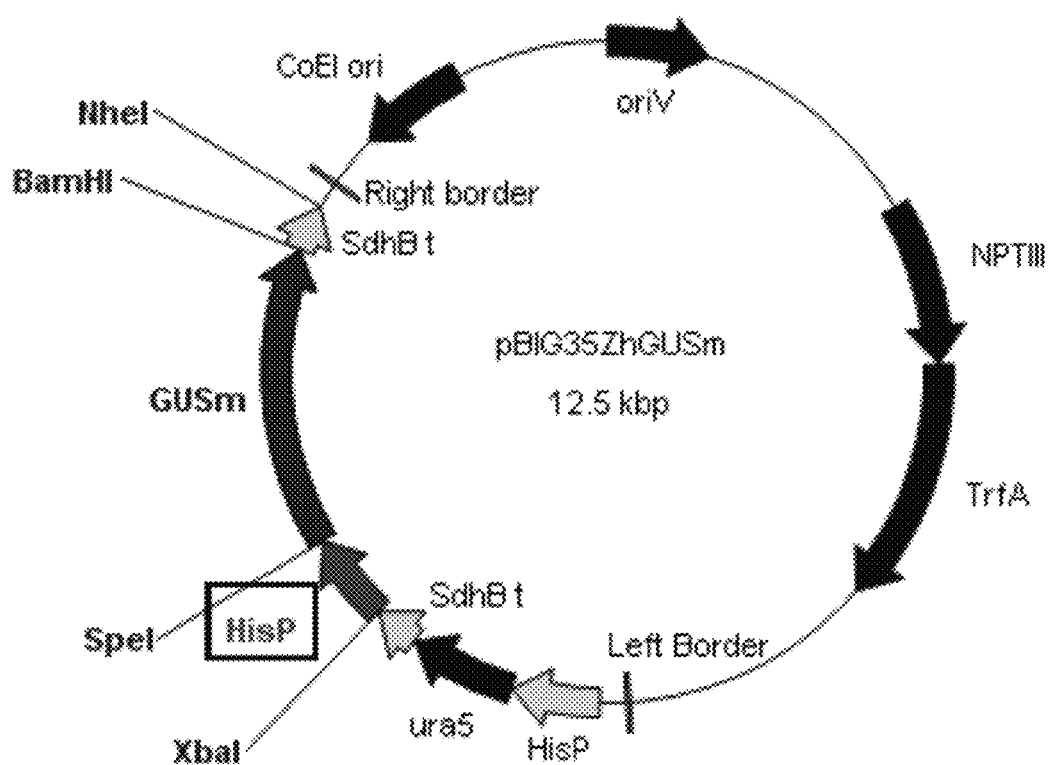
FIG. 1 shows an example of a vector for use in evaluation of the promoter of the present invention. The HisP sequence is replaced with the promoter of the present invention before use.

The present invention will be described in more detail below. The following embodiments are illustrated to describe the present invention, and it is not intended to limit the present invention only to these embodiments. The present invention can be implemented in various modes, without departing from the spirit of the present invention.

It should be noted that all publications cited herein, including prior art documents, patent gazettes and other patent documents, are incorporated herein by reference. Moreover, this specification incorporates the contents disclosed in the specification and drawings of Japanese Patent Application No. 2013-066265 (filed on Mar. 27, 2013), based on which the present application claims priority.

Unless otherwise specified herein, nucleotide sequences are shown such that their 5'-terminal end is on the left-hand side and their 3'-terminal end is on the right-hand side.

1. Promoters

The inventors of the present invention have succeeded, ahead of others, in cloning several types of promoter sequences from a lipid-producing fungus, *M. alpina*, as described in more detail later in the Example section. Moreover, the inventors of the present invention have also confirmed that proteins expressed under these promoters exert their biological activity.

Promoters according to the present invention are PP7p, CIT1p, PP3p, PP2p, PP6ps, HSC82p, SSA2p, GAL10-2p and/or partial sequences (truncated sequences) thereof. These promoter region sequences and truncated sequences thereof are shown in the table below.

Any one sequence selected from the nucleotide sequences shown in the table, i.e., any one sequence selected from the group consisting of SEQ ID NOs: 1 to 28 is hereinafter referred to as "the promoter sequence of the present invention."

TABLE 1

| Promoter sequence: Name (SEQ ID NO) | Truncated promoter sequence: Name (SEQ ID NO) | | | |
|---|---|---|---|---|
| PP7p (SEQ ID NO: 1) | PP7p D1000 (SEQ ID NO: 2) | PP7p D750 (SEQ ID NO: 3) | PP7p D500 (SEQ ID NO: 4) | |
| CIT1p (SEQ ID NO: 5) | CIT1p D1300 (SEQ ID NO: 6) | CIT1p D1000 (SEQ ID NO: 7) | CIT1p D700 (SEQ ID NO: 8) | CIT1p D400 (SEQ ID NO: 9) |
| PP3p (SEQ ID NO: 10) | PP3p D1600 (SEQ ID NO: 11) | PP3p D1200 (SEQ ID NO: 12) | | |
| PP2p (SEQ ID NO: 13) | | | | |
| PP6p (SEQ ID NO: 14) | PP6p D1000 (SEQ ID NO: 15) | PP6p D750 (SEQ ID NO: 16) | | |
| HSC82p (SEQ ID NO: 17) | HSC82p D800 (SEQ ID NO: 18) | HSC82p D600 (SEQ ID NO: 19) | HSC82p D400 (SEQ ID NO: 20) | HSC82p D200 (SEQ ID NO: 21) |
| SSA2p (SEQ ID NO: 22) | SSA2p D850 (SEQ ID NO: 23) | SSA2p D600 (SEQ ID NO: 24) | SSA2p D400 (SEQ ID NO: 25) | SSA2p D200 (SEQ ID NO: 26) |
| GAL10-2p (SEQ ID NO: 27) | GAL10-2p D2000 (SEQ ID NO: 28) | | | |

Thus, the present invention provides the following polynucleotide as a promoter showing high expression activity in cells of microorganisms belonging to the genus *Mortierella*.

A polynucleotide of any one selected from the group consisting of (a) to (c) shown below:
(a) a polynucleotide which contains the promoter sequence of the present invention;
(b) a polynucleotide which has a nucleotide sequence sharing an identity of 90% or more with the promoter sequence of the present invention and which shows promoter activity in cells of microorganisms belonging to the genus *Mortierella*; and
(c) a polynucleotide which is hybridizable under stringent conditions with a polynucleotide consisting of a nucleotide sequence complementary to the promoter sequence of the present invention and which shows promoter activity in cells of microorganisms belonging to the genus *Mortierella*.

The above polynucleotides shown in (a) to (c) are each hereinafter referred to as "the polynucleotide of the present invention."

Moreover, in the context of the present invention, "having" the promoter sequence of the present invention means "comprising" the promoter sequence of the present invention. Thus, an additional sequence(s) (e.g., an enhancer sequence) other than the promoter sequence of the present invention may be added to the upstream (5'-terminal side) or downstream (3'-terminal side) of the promoter sequence of the present invention. Such an additional sequence may be added to the promoter sequence of the present invention via a nucleotide sequence of 1 to 1000 bp, 1 to 900 bp, 1 to 800 bp, 1 to 700 bp, 1 to 600 bp, 1 to 500 bp, 1 to 400 bp, 1 to 300 bp, 1 to 200 bp, 1 to 100 bp, 1 to 75 bp, 1 to 50 bp, 1 to 25 by or 1 to 10 bp, or alternatively, may be directly added to the promoter sequence of the present invention (i.e., the number of nucleotide residues located between the promoter sequence of the present invention and the additional sequence is zero).

As used herein, the term "polynucleotide" is intended to mean DNA or RNA.

As used herein, the expression "polynucleotide which is hybridizable under stringent conditions" is intended to mean, for example, a polynucleotide that can be obtained by means of, e.g., colony hybridization, plaque hybridization or Southern hybridization using, as a probe, the whole or a part of a polynucleotide consisting of a nucleotide sequence complementary to the promoter sequence of the present invention. For hybridization, it is possible to use techniques as described in, e.g., "Sambrook & Russell, Molecular Cloning: A Laboratory Manual Vol. 3, Cold Spring Harbor, Laboratory Press 2001" and "Ausubel, Current Protocols in Molecular Biology, John Wiley & Sons 1987-1997."

As used herein, the term "high stringent conditions" is intended to mean, for example, conditions of (1) 5× SSC, 5× Denhardt's solution, 0.5% SDS, 50% formamide and 50° C., (2) 0.2× SSC, 0.1% SDS and 60° C., (3) 0.2× SSC, 0.1% SDS and 62° C., (4) 0.2× SSC, 0.1% SDS and 65° C., or (5) 0.1× SSC, 0.1% SDS and 65° C., without being limited thereto. Under these conditions, it can be expected that DNA having a higher sequence identity is more efficiently obtained at a higher temperature. However, the stringency of hybridization would be affected by a plurality of factors, including temperature, probe concentration, probe length, ionic strength, reaction time, salt concentration and so on. Those skilled in the art would be able to achieve the same stringency by selecting these factors as appropriate.

It should be noted that if a commercially available kit is used for hybridization, an Alkphos Direct Labelling and Detection System (GE Healthcare) may be used for this purpose, by way of example. In this case, hybridization may be accomplished in accordance with the protocol attached to the kit, i.e., a membrane may be incubated overnight with a labeled probe and then washed with a primary washing buffer containing 0.1% (w/v) SDS under conditions of 55° C. to detect the hybridized DNA. Alternatively, if a commercially available reagent (e.g., PCR labeling mix (Roche Diagnostics)) is used for digoxigenin (DIG) labeling of a probe during probe preparation based on the whole or a part of a nucleotide sequence complementary to the promoter sequence of the present invention, a DIG nucleic acid detection kit (Roche Diagnostics) may be used for detection of hybridization.

In addition to those listed above, other hybridizable polynucleotides include polynucleotides sharing an identity of 90% or more, 91% or more, 92% or more, 93% or more, 94% or more, 95% or more, 96% or more, 97% or more, 98% or more, 99% or more, 99.1% or more, 99.2% or more, 99.3% or more, 99.4% or more, 99.5% or more, 99.6% or more, 99.7% or more, 99.8% or more, or 99.9% or more with the promoter sequence of the present invention, as calculated by homology search software such as FASTA or BLAST using default parameters.

It should be noted that the identity of nucleotide sequences can be determined by using FASTA (Science 227 (4693): 1435-1441, (1985)) or the algorithm of Karlin and Altschul, BLAST (Basic Local Alignment Search Tool) (Proc. Natl. Acad. Sci. USA 872264-2268, 1990; Proc Natl Acad Sci USA 90: 5873, 1993). Based on the algorithm of BLAST, programs called blastn, blastx, tblastn and tblastx have been developed (Altschul S F, et al: J Mol Biol 215: 403, 1990). If blastn is used for nucleotide sequence analysis, parameters may be set to, for example, score=100 and wordlength=12. If BLAST and Gapped BLAST programs are used, default parameters in each program may be used.

In the context of the present invention, the term "promoter activity" is intended to mean that when a protein-encoding gene sequence (hereinafter referred to as a "target gene") is inserted downstream of the promoter of the present invention, an expression product of this gene is obtained.

The term "expression product" used here is intended to mean either or both of RNA (e.g., hnRNA, mRNA, siRNA or miRNA) which is a transcribed product of the gene and a protein which is a translated product of the gene.

Insertion of a target gene may be accomplished such that the 5'-terminal end of the target gene is located in a region within 500 bp, 400 bp, 300 bp, 200 bp, 100 bp, 50 bp, 30 by or 10 by from the 3'-terminal end of the promoter sequence of the present invention.

In the case of attempting to confirm the activity of the promoter sequence of the present invention, the target gene is not limited in any way, but is preferably a gene encoding a protein whose activity can be measured by the established method.

Examples of such a gene include, but are not limited to, selection marker genes such as neomycin resistance gene, hygromycin B phosphotransferase gene and so on, as well as expression reporter genes such as LacZ, GFP (Green Fluorescence Protein) and luciferase genes, etc.

Preferably, confirmation of promoter activity may be accomplished by using a gene for β-D-glucuronidase (GUS) to measure GUS activity. In cases where *M. alpina* is used as a host, the GUS gene is preferably a GUSm gene whose codon usage frequency has been adapted to *M. alpina*.

GUS activity can be measured as follows: the promoter sequence of the present invention is used to cause GUS gene expression in cells of microorganisms belonging to the genus *Mortierella*, the GUS protein collected from the above cells is then reacted with p-nitrophenyl-β-D-glucuronide, and the reaction system is measured over time for absorbance at a wavelength of 405 nm, followed by calculation from the measured values according to the following equation.

$$\text{GUS activity (nmol/(mg·min))}=1000\times[(\text{gradient value in the absorbance versus time graph obtained for each sample})/(\text{gradient value in the calibration graph})]/[(\text{protein concentration in the sample})/5]$$

The GUS gene used for this purpose is generally the *E. coli*-derived GUS gene (CDS sequence: SEQ ID NO: 29, amino acid sequence: SEQ ID NO: 30). In cases where the promoter sequence of the present invention is used to cause GUS gene expression in cells of microorganisms belonging to the genus *Mortierella*, a GUSm gene (CDS sequence: SEQ ID NO: 31, amino acid sequence: SEQ ID NO: 32) may be used, which has been modified such that the codon usage in the *E. coli*-derived GUS gene is adapted to microorganisms of the genus *Mortierella*.

Figure 12A:
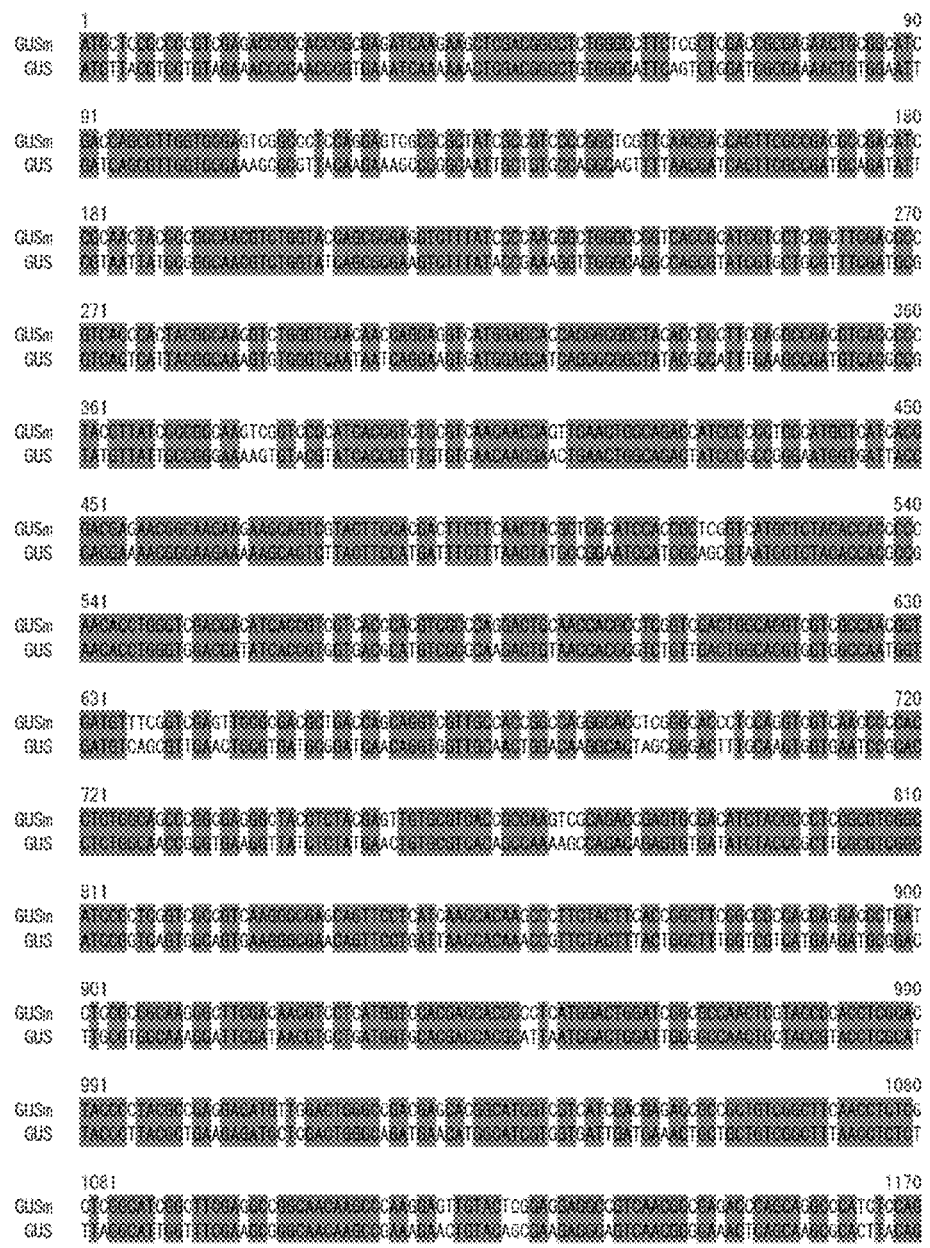
FIG. 12A shows an alignment between *E. coli*-derived GUS gene (CDS sequence: SEQ ID NO: 29, amino acid sequence: SEQ ID NO: 30) and GUSm gene (CDS sequence: SEQ ID NO: 31, amino acid sequence: SEQ ID NO: 32) which has been modified such that the codon usage in the *E. coli*-derived GUS gene is adapted to microorganisms of the genus *Mortierella*.
Figure 12B:
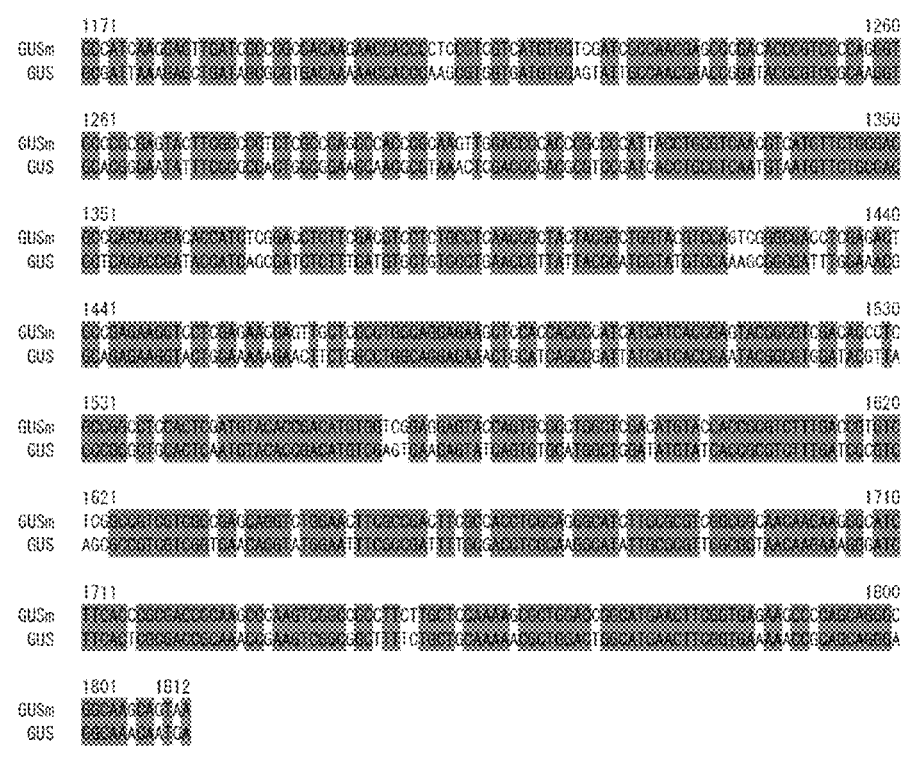

As for examples of codon usage modification, reference may be made to the alignment between GUSm and GUS shown in FIG. 12A and FIG. 12B.

The promoter activity in the present invention is preferably intended to give GUS protein activity of at least 500, 600, 700, 800, 900, 1000, 1200, 1400, 1600, 1800 or 2000 nmol/(mg·min) upon expression of the GUS reporter gene in cells of microorganisms belonging to the genus *Mortierella* as described above.

Procedures for gene transfer into host cells are as described later.

The polynucleotide of the present invention mentioned above can be obtained by known genetic engineering procedures or known synthesis procedures.

2. Vectors and Transformants

In another embodiment, the present invention also provides an expression vector containing the polynucleotide of the present invention (hereinafter referred to as "the vector of the present invention").

The vector of the present invention is generally configured to comprise:
(i) the promoter of the present invention; and
(ii) an expression cassette comprising, as constituent elements, signals that function in host cells for transcription termination and polyadenylation of an RNA molecule.

The thus configured vector is introduced into host cells. Examples of appropriate host cells used in the present invention include lipid-producing fungi, yeast and so on.

As lipid-producing fungi, strains as found in MYCO-TAXON, Vol. XLIV, No. 2, pp. 257-265 (1992) can be used. Specific examples include microorganisms belonging to the genus *Mortierella*, as exemplified by microorganisms belonging to the subgenus *Mortierella* such as *Mortierella elongata* IFO8570, *Mortierella exigua* IFO8571, *Mortierella hygrophila* IFO5941, *Mortierella alpina* IFO8568, ATCC16266, ATCC32221, ATCC42430, CBS 219.35, CBS224.37, CBS250.53, CBS343.66, CBS527.72, CBS528.72, CBS529.72, CBS608.70, CBS754.68, etc., as well as microorganisms belonging to the subgenus *Micromucor* such as *Mortierella isabellina* CBS194.28, IFO6336, IFO7824, IFO7873, IFO7874, IFO8286, IFO8308, IFO7884, *Mortierella nana* IFO8190, *Mortierella ramanniana* IFO5426, IFO8186, CBS 112.08, CBS212.72, IFO7825, IFO8184, IFO8185, IFO8287, *Mortierella vinacea* CBS236.82, etc. Particularly preferred is *Mortierella alpina*.

Such a vector may be prepared starting from an existing expression vector, e.g., pDura5 (Appl. Microbiol. Biotechnol., 65, 419-425, (2004)), pBIG35 (Appl. Environ. Microbiol., (2009), vol. 75, p. 5529-5535), pD4 (Appl. Environ. Microbiol., November 2000, 66 (11), p. 4655-4661), pDZeo (J. Biosci. Bioeng., December 2005, 100 (6), p. 617-622), pDX vector (Curr. Genet., 2009, 55 (3), p. 349-356) or pBIG3ura5 (Appl. Environ. Microbiol., 2009, 75, p. 5529-5535) by replacement of the promoter region in the starting expression vector with the promoter sequence of the present invention, although the starting expression vector is not limited to the above vectors.

For transformation of host cells, a selection marker may be used to confirm whether the vector has been introduced. Examples of a selection marker available for use include auxotrophic markers (ura5, niaD, trp1), drug resistance markers (hygromycine, zeocin), geneticin resistance gene (G418r), copper resistance gene (CUP1) (Marin et al., Proc. Natl. Acad. Sci. USA, 81, 337 1984), cerulenin resistance genes (fas2m, PDR4) (Junji Inokoshi et al., Biochemistry, vol. 64, p. 660, 1992; Hussain et al., gene, 101, 149, 1991), etc.

Examples of auxotrophic markers include, but are not limited to, (1) to (15) shown below:

(1) methionine auxotrophic marker: met1, met2, met3, met4, met5, met6, met7, met8, met10, met13, met14 or met20;
(2) tyrosine auxotrophic marker: tyr1 or isoleucine;
(3) valine auxotrophic marker: ilv1, ilv2, ilv3 or ilv5;
(4) phenylalanine auxotrophic marker: pha2;
(5) glutamic acid auxotrophic marker: glu3;
(6) threonine auxotrophic marker: thr1 or thr4;
(7) aspartic acid auxotrophic marker: asp1 or asp5;
(8) serine auxotrophic marker: ser1 or ser2;
(9) arginine auxotrophic marker: arg1, arg3, arg4, arg5, arg8, arg9, arg80, arg81, arg82 or arg84;
(10) uracil auxotrophic marker: ura1, ura2, ura3, ura4, ura5 or ura6;
(11) adenine auxotrophic marker: ade1, ade2, ade3, ade4, ade5, ade6, ade8, ade9, ade12 or ADE15;
(12) lysine auxotrophic marker: lys1, lys2, lys4, lys5, lys7, lys9, lys11, lys13 or lys14;
(13) tryptophan auxotrophic marker: trp1, trp2, trp3, trp4 or trp5;
(14) leucine auxotrophic marker: leu1, leu2, leu3, leu4 or leu5; and
(15) histidine auxotrophic marker: his1, his2, his3, his4, his5, his6, his7 or his8.

Examples of drug resistance markers include, but are not limited to, hygromycin (Hygromycin B) resistance gene, bleomycin t (pleomycin) resistance gene (Transformation of filamentous fungi based on hygromycin b and phleomycin resistance markers, Methods in Enzymology, Volume 216, 1992, Pages 447-457, Peter J. Punt, Cees A. M. J. J. van den Hondel), bialaphos resistance gene (Avalos, J., Geever, R. F., and Case, M. E. 1989. Bialaphos resistance as a dominant selectable marker in *Neurospora crassa*. Curr. Genet. 16: 369-372), sulfonylurea resistance gene (Zhang, S., Fan, Y., Xia, Y. X., and Keyhani, N. O. (2010) Sulfonylurea resistance as a new selectable marker for the entomopathogenic fungus *Beauveria bassiana*. Appl Microbiol Biotechnol 87: 1151-1156), benomyl resistance gene (Koenraadt, H., S. C. Sommerville, and A. L. Jones. 1992. Characterization of mutations in the beta-tubulin gene of benomyl-resistant field strains of *Venturia inaequalis* and other pathogenic fungi. Mol. Plant Pathol. 82:1348-1354), acetamide assimilation gene (Acetamidase, AmdS) (Kelly, J. M. and Hynes, M. J. (1985). Transformation of *Aspergillus niger* by the Eamds gene of *Aspergillus nidulans*. EMBO J. 4, 475-479), etc.

For transformation of host cells, commonly used known techniques can be used. For example, in the case of lipid-producing fungi, it is possible to use electroporation (Mackenzie D. A. et al. Appl. Environ. Microbiol., 66, 4655-4661, 2000), particle delivery method (described in JP 2005-287403 A entitled "Breeding Method of Lipid Producing Fungi") or *Agrobacterium*-mediated method, without being limited thereto.

In addition, as for standard cloning techniques, reference may be made to "Sambrook & Russell, Molecular Cloning: A Laboratory Manual Vol. 3, Cold Spring Harbor Laboratory Press 2001" and "Methods in Yeast Genetics, A laboratory manual (Cold Spring Harbor Laboratory Press, Cold Spring Harbor, N.Y.)," etc.

3. Method for Production of Proteins, Lipids or Fatty Acids

In yet another embodiment, the present invention also provides a method for production of proteins, lipids or fatty acids using the above transformant.

A target gene is highly expressed in a non-human transformant transformed with the promoter of the present invention (hereinafter referred to as "the transformant of the present invention"), particularly prepared using a microorganism belonging to the genus *Mortierella* as a host cell.

Thus, when using the transformant of the present invention, a target protein can be produced efficiently.

For example, a target gene is operably introduced into the vector of the present invention and a transformant transformed with this vector is cultured, whereby a target protein can be expressed from the target gene in cells of the transformant.

The expressed target protein may be collected, for example, by preparing a cell lysate from the transformant and treating this lysate in accordance with known procedures. For details of target protein collection, reference may be made to "Sambrook & Russell, Molecular Cloning: A Laboratory Manual Vol. 3, Cold Spring Harbor Laboratory Press 2001" and "Methods in Yeast Genetics, A laboratory manual (Cold Spring Harbor Laboratory Press, Cold Spring Harbor, N.Y.)," etc.

The target gene is not limited in any way, but is preferably a gene encoding a lipid synthase (hereinafter referred to as a "lipid synthase gene"). Examples include genes encoding acyl-CoA synthase, glycerol-3-phosphate acyltransferase, diacylglycerol acyltransferase, fatty acid elongase, Δ9 fatty acid desaturase gene, Δ12 fatty acid desaturase gene, Δ6 fatty acid desaturase gene, Δ5 fatty acid desaturase gene, Δ4 fatty acid desaturase gene, ω3 fatty acid desaturase gene, lysophospholipid acyltransferase gene, phosphatidic acid phosphatase gene, fatty acid synthase gene, acetyl-CoA carboxylase gene, and ATP:citrate lyase gene.

When cells with lipid synthesis ability, e.g., a lipid-producing fungus or the like is used as a host to express a lipid synthase gene, the lipid synthase expressed from this gene causes synthesis of lipids and/or fatty acids, which may then be collected. Thus, upon culturing the transformant of the present invention, it is possible to produce lipids and/or fatty acids with high efficiency.

Lipids or fatty acids can be extracted as follows from cells which have been transformed in accordance with the present invention. After being cultured, a transformed strain of an organism (e.g., lipid-producing fungus or yeast) is treated in a standard manner, e.g., by centrifugation or filtration to obtain cultured cells. The cells are washed well with water and preferably further dried. Drying may be accomplished by freeze-drying, air-drying, etc. The dried cells are optionally homogenized, e.g., with a Dynomil or by ultrasonication, and then extracted with an organic solvent preferably under a nitrogen stream. Organic solvents used for this purpose include ether, hexane, methanol, ethanol, chloroform, dichloromethane, petroleum ether and so on. Alternatively, good results can also be obtained by alternating extraction with methanol and petroleum ether or by extraction with a single-phase solvent system of chloroform-methanol-water. When the organic solvent is distilled off from the extract under reduced pressure, fatty acid-containing lipids can be obtained. The extracted fatty acids may be converted into corresponding methyl esters by the hydrochloric acid-methanol method, etc.

Moreover, fatty acids can be separated in a state of mixed fatty acids or mixed fatty acid esters from the above fatty acid-containing lipids by concentration and separation in a standard manner (e.g., urea addition, separation under cooling, column chromatography).

EXAMPLES

The present invention will now be described in more detail by way of the following examples, which are not intended to limit the scope of the present invention.
Genomic Analysis of *Mortierella alpina*

*M. alpina* strain 1S-4 was inoculated into 100 ml of GY2:1 medium (2% glucose, 1% yeast extract, pH 6.0) and cultured at 28° C. for 2 days under shaking conditions. The cells were collected by filtration, and their genomic DNA was prepared using DNeasy (QIAGEN).

The nucleotide sequence of the above genomic DNA was determined using a Roche 454 GS FLX Standard, during which nucleotide sequencing was conducted in two runs for a fragment library and in three runs for a mate-paired library. The resulting nucleotide sequences were assembled to give 300 super contigs.
Expression Analysis

*M. alpina* strain 1S-4 was inoculated into 100 ml of a medium (1.8% glucose, 1% yeast extract, pH 6.0) and pre-cultured for 3 days at 28° C. A 10 L culture vessel (Able Co., Tokyo) was charged with 5 L of a medium (1.8% glucose, 1% soybean meal, 0.1% olive oil, 0.01% Adekanol, 0.3% $KH_2PO_4$, 0.1% $Na_2SO_4$, 0.05% $CaCl_2.H_2O$, 0.05% $MgCl_2.6H_2O$, pH 6.0) and inoculated with the entire pre-cultured product, followed by aerobic spinner culture under conditions of 300 rpm, 1 vvm and 26° C. for 8 days. On days 1, 2 and 3 of culture, glucose was added in an amount corresponding to 2%, 2% and 1.5%, respectively. The cells were collected at each stage of culture (day 1, 2, 3, 6 or 8) to prepare total RNA by the guanidine hydrochloride/CsCl method. Using SOLiD™ Total RNA-Seq for Whole Transcriptome Libraries (Applied Biosystems), cDNA was synthesized for each stage and sequenced in SOLiD.
Cloning of Promoter Regions Cloning was performed as follows on promoter regions in genes whose expression levels were considered to be high in *M. alpina* strain 1S-4 in light of the results of expression analysis or a promoter region in a homolog of the galactose metabolic system gene.

First, primers required for PCR amplification of each promoter region were designed as follows. It should be noted that the underlined parts in the nucleotide sequences of primers shown below each represent a restriction enzyme recognition site. Primers were designed such that XbaI and SpeI recognition sequences were added respectively to both ends of the promoter region. However, only for GAL10-2p which has a SpeI recognition sequence in its sequence, primers were designed such that an XbaI recognition sequence was added to each end. The symbol "F" or "R" appearing in each primer name denotes that the primer is a forward primer or a reverse primer, respectively.

```
Promoter PP7p
PP7p F XbaI
                                  (SEQ ID NO: 33)
AATATCTAGATGACCGTGCGCTTTTTGAGAC PP7p R SpeI
                                  (SEQ ID NO: 34)
AGCAACTAGTCGTATATTTGTTGAAAGGTG Promoter CIT1p
CIT1p F XbaI
                                  (SEQ ID NO: 35)
ATTTTCTAGACACCTCAAAAACGTGCCTTG CIT1p R SpeI
                                  (SEQ ID NO: 36)
AATAACTAGTGGCGGATATGTGTATGGAG Promoter PP3p
PP3p F XbaI
                                  (SEQ ID NO: 37)
AACGTCTAGACGTGTTATCTTGCGCTGC
```

-continued

```
PP3p R SpeI
                                      (SEQ ID NO: 38)
TCATACTAGTGATGATTTAGAGGTGTTGG

Promoter PP2p
PP2p F XbaI
                                      (SEQ ID NO: 39)
AAGCTCTAGAGACTGTAAAGACGGAGGGG PP2p R SpeI
                                      (SEQ ID NO: 40)
AGTAACTAGTTGTGGATAGTGGGTAGTGG Promoter PP6ps
PP6ps F XbaI
                                      (SEQ ID NO: 41)
AAAGTCTAGACTGGCAATAGTTAGTGCACG PP6ps R SpeI
                                      (SEQ ID NO: 42)
ATCAACTAGTGATGGAGGTTTGTTTGAGAAG Promoter HSC82p
HSC82p F XbaI
                                      (SEQ ID NO: 43)
ATCATCTAGAGAGCTCAAGATGAAGGTGCTC HSC82p R SpeI
                                      (SEQ ID NO: 44)
AATAACTAGTGGTGTGTGTGGTTTGCGGG Promoter SSA2p
SSA2p F XbaI
                                      (SEQ ID NO: 45)
TTAGTCTAGAAAAGTGCTGCTTCGGAACC SSA2p R SpeI
                                      (SEQ ID NO: 46)
AGATACTAGTGATGTAGATGTGAGTGTGAG Promoter GAL10-2p
GAL10-2p F XbaI
                                      (SEQ ID NO: 47)
AATATCTAGAGGTTCCGAGAGGTGGATTTG GAL10-2p R XbaI
                                      (SEQ ID NO: 48)
ATAATCTAGATGGCTCCTGAAAGGACGAG
```

Using the genome of *Mortierella alpina* strain 1S-4 as a template, each promoter region was cloned by PCR. The polymerase used was PrimeSTAR GXL (TaKaRa).

Vector Construction for Promoter Evaluation

GUSm gene (SEQ ID NO: 31) which had been modified such that the codon usage in the *E. coli*-derived GUS gene (SEQ ID NO: 29) was adapted to microorganisms of the genus *Mortierella* (FIG. 12A and FIG. 12B) was used as a reporter gene.

GUSm was ligated to plasmid pBIG35 containing histone promoter (HisP) serving as a constitutive expression promoter (Appl. Environ. Microbiol., (2009), vol. 75, p. 5529-5535) to construct an expression cassette. This expression cassette was further ligated in tandem to a uracil auxotrophic marker gene (ura5) to construct a binary vector for transformation, pBIG35ZhGUSm (FIG. 1). It should be noted that the GUSm gene used in the vector is an artificially synthesized β-D-glucuronidase gene whose codon usage frequency has been adapted to *M. alpina*. Ura5 is the *M. alpina* orotate phosphoribosyltransferase gene. HisP is a promoter for the *M. alpina* histone H4.1 gene. SdhBt is a terminator for the *M. alpina* succinate dehydrogenase gene. ColE1 ori is the origin of replication, NPTII is a kanamycin resistance gene, TrfA is a gene responsible for plasmid amplification, and Left and Right borders are repeat sequences for gene transfer.

The promoter regions cloned as described above were each excised with restriction enzymes XbaI and SpeI or with a restriction enzyme XbaI, and then inserted in place of HisP into the XbaI- and SpeI-digested vector pBIG35ZhGUSm.

Transformation of *Mortierella alpina*

A uracil auxotrophic strain (Δura-3) was induced from *M. alpina* strain 1S-4 in accordance with procedures described in a patent document (WO2005/019437) and cultured on 0.05 mg/mL uracil-containing Czapek-Dox agar medium (3% sucrose, 0.2% $NaNO_3$, 0.1% $KH_2PO_4$, 0.05% KCl, 0.05% $MgSO_4 \cdot 7H_2O$, 0.001% $FeSO_4 \cdot 7H_2O$, 2% agar, pH 6.0). The cultured product thus obtained was collected and filtered through Miracloth (Calbiochem) to prepare a spore suspension of *M. alpina* Δura-3. *Agrobacterium* (*Agrobacterium tumefaciens* C58C1) was transformed with each of the prepared vectors for promoter evaluation by electroporation and cultured at 28° C. for 48 hours on LB-Mg agar medium (1% tryptone, 0.5% yeast extract, 85 mM NaCl, 0.5 mM $MgSO_4 \cdot 7H_2O$, 0.5 mM NaOH, 1.5% agar, pH 7.0). *Agrobacterium* transformants carrying the vectors were confirmed by PCR. *Agrobacterium* transformants carrying the vectors were cultured at 28° C. at 120 rpm for 2 days under shaking conditions in 100 mL of MM medium (10 mM $K_2HPO_4$, 10 mM $KH_2PO_4$, 2.5 mM NaCl, 2 mM $MgSO_4 \cdot 7H_2O$, 0.7 mM $CaCl_2$, 9 μM $FeSO_4 \cdot 7H_2O$, 4 mM $(NH_4)_2SO_4$, 10 mM glucose, pH 7.0), centrifuged at 5,800× g and then diluted with fresh IM medium (MM medium supplemented with 0.5% glycerol, 200 μM acetosyringone and 40 mM 2-(N-morpholino) ethanesulfonic acid (MES) and adjusted to pH 5.3) to prepare suspensions. These suspensions were cultured for 8 to 12 hours at 28° C. at 300 rpm under shaking conditions to reach OD 660=0.4 to 3.7. Each of the cell suspensions (100 μL) was mixed with an equal volume of the above *M. alpina* Δura-3 suspension ($10^8$ $mL^{-1}$), spread onto a nitrocellulose membrane (70 mm diameter; hardened low-ash grade 50, Whatman) placed on a co-culture medium (having the same composition as IM medium, except for containing 5 mM glucose instead of 10 mM glucose and 1.5% agar) and then cultured at 23° C. for 2 to 5 days. After co-culture, the membrane was transferred onto uracil-free and 0.03% Nile blue A (Sigma)-containing SC agar medium (5.0 g Yeast Nitrogen Base w/o Amino Acids and Ammonium Sulfate (Difco), 1.7 g $(NH_4)_2SO_4$, 20 g glucose, 20 mg adenine, 30 mg tyrosine, 1.0 mg methionine, 2.0 mg arginine, 2.0 mg histidine, 4.0 mg lysine, 4.0 mg tryptophan, 5.0 mg threonine, 6.0 mg isoleucine, 6.0 mg leucine, 6.0 mg phenylalanine, 20 g/L agar) and cultured at 28° C. for 5 days. Hyphae from visible fungal colonies were transferred onto uracil-free SC medium. Transfer onto fresh uracil-free SC medium was repeated twice to thereby select transformants stably retaining their traits.

Selection of High Expression Promoters

Culture and Collection of Strains

Each transformant was cultured at 28° C. for 2 days on GY agar medium (2% glucose, 1% yeast extract, 1.5% agar). After completion of the culture, the cells were collected by being scraped off together with the agar.

Protein Extraction From Cells

The collected cells were mixed with 500 μL of a homogenization buffer (100 mM Tris-HCl (pH 8.0), 5 mM 2-mercaptoethanol) and homogenized twice at 5000 rpm for 30 seconds with a TOMY beads shocker using glass beads of 0.1 mm diameter. The homogenate was centrifuged at 8000× g for 10 minutes and the collected supernatant was further centrifuged at 20400× g for 10 minutes to collect the supernatant as a protein solution. The collected solution was measured for its protein concentration and optionally diluted to any concentration with the homogenization buffer. The foregoing operations were all conducted on ice.

GUS Activity Measurement

A substrate (p-nitrophenyl-β-D-glucuronide) was dissolved in an assay buffer (21.7 mM $NaH_2PO_4$, 33.9 mM $Na_2HPO_4$, 1.11 mM EDTA (pH 8.0)) to give a final concentration of 1.25 mM. This substrate solution (160 μL) and each protein sample (40 μL) were mixed on a 96-well microtiter plate, and the absorbance at 405 nm was measured over time at 37° C. The absorbance of p-nitrophenol was measured at 0.05 mM, 0.1 mM, 0.2 mM and 0.5 mM to prepare a calibration curve, and the value of GUS activity in each sample was calculated according to the following equation.

GUS activity (nmol/(mg·min))=1000×[(gradient value in the absorbance versus time graph obtained for each sample)/(gradient value in the calibration graph)]/[(protein concentration in the sample)/5]

The amount (nmol) of p-nitrophenyl-β-D-glucuronide converted into p-nitrophenol by the action of 1 mg/mL protein for 1 minute is defined as 1 unit of GUS activity.

Selection of Strains for GUS Activity Evaluation

The stable transformed strains (30 strains) selected for evaluation of each promoter were cultured on GY agar medium as described above and measured for their GUS activity. From among these 30 strains, 10 strains showing moderate GUS activity were selected.

Evaluation of Promoter Activity

Figure 2:
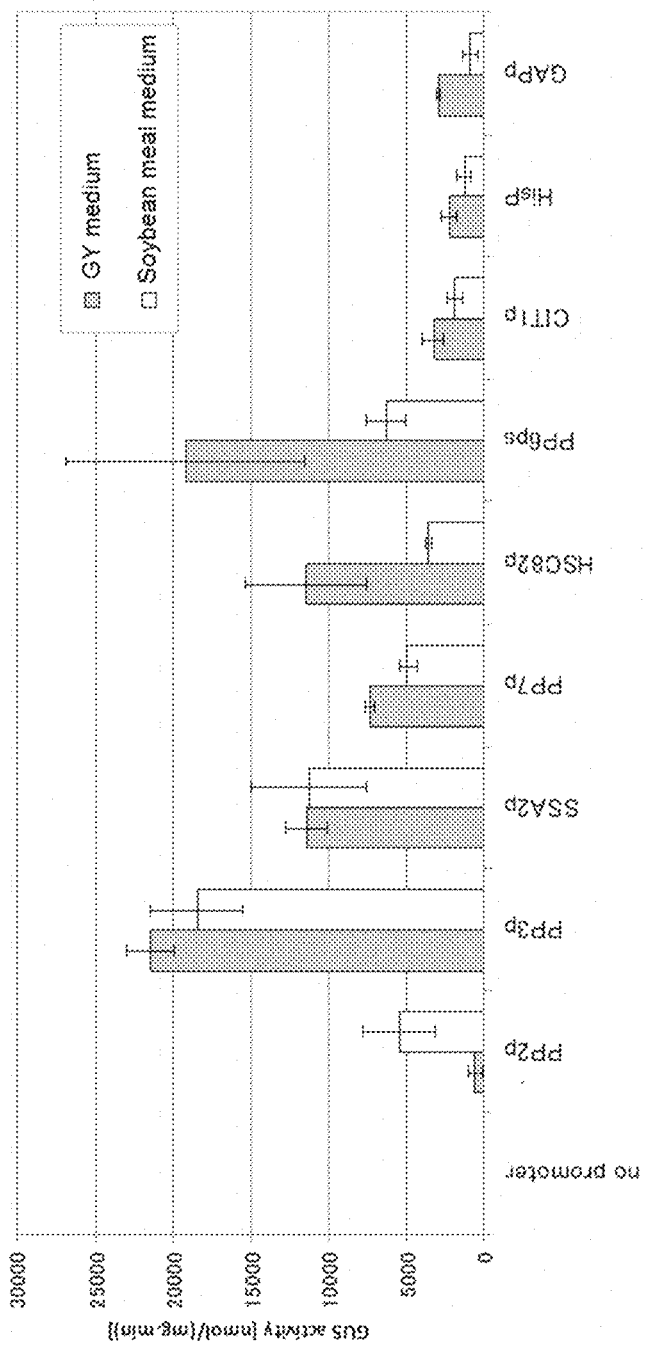
FIG. 2 shows the promoter activity in transformants transformed with the promoter sequences of the present invention upon culture in various media (gray bar: GY medium, white bar: soybean meal medium). Culture was conducted in each medium (10 ml) at 28° C. at 300 rpm for 5 days.

The selected strains were cultured at 28° C. at 300 rpm for 5 days under shaking conditions in GY liquid medium (10 ml) or soybean meal medium (10 ml). After completion of the culture, the cells were collected by filtration and measured for their GUS activity. The mean of the measured values was evaluated as the activity of the promoter. The results obtained are shown in FIG. 2.

The evaluated promoters were found to have higher promoter activity than known *Mortierella*-derived promoters, HisP and GAPp, in the GY medium and/or in the soybean meal medium.

Study on Culture Time and the Activity of Each Promoter

To determine culture time-induced changes in promoter activity, the strains selected for each promoter were cultured at 28° C. under shaking conditions in GY liquid medium (10 ml) for 2 days, 5 days, 7 days or 14 days. After completion of the culture, the cells were collected by filtration and measured for their GUS activity. The results obtained are shown in the table below.

TABLE 2

Number of days for culture and activity of each promoter

| Promoter name | GUS activity (nmol/(min · $mg_{protein}$)) | | | |
|---|---|---|---|---|
| | 2 days | 5 days | 7 days | 14 days |
| PP7p | 10000 | | 10000 | 10000 |
| CIT1p | 7000 | | 2000 | 1000 |
| PP3p | 2500 | | 28000 | 30000 |
| PP2p | 1000 | | 1000 | 4500 |
| PP6p | 10000 | 20000 | | 2500 |
| HSC82p | 10000 | | 10000 | 6000 |
| SSA2p | 12000 | | 10000 | 14000 |
| GAPp | 3000 | | 2500 | 2500 |
| HisP | 2500 | | 2500 | 2500 |

Evaluation of Inducible Promoter

Promoter GAL10-2p was evaluated as follows.

Figure 3:
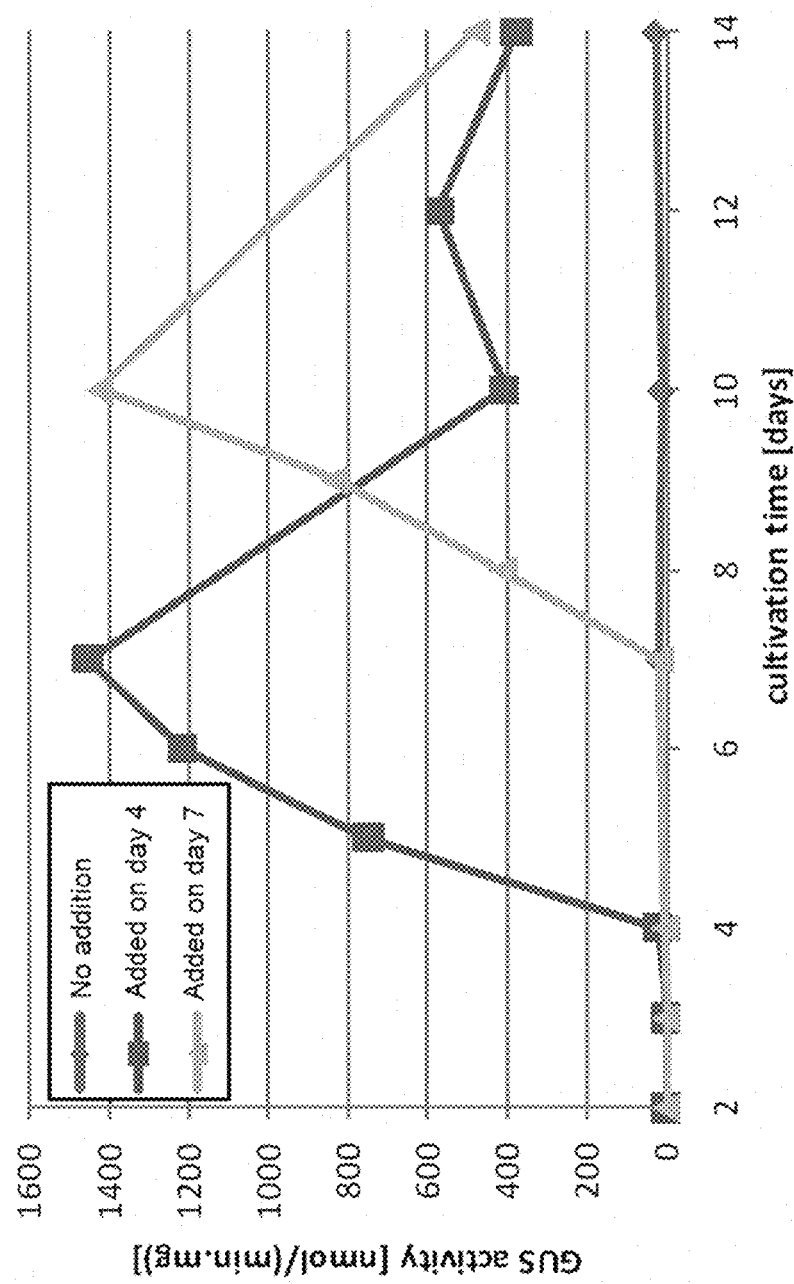
FIG. 3 shows the activity of promoter GAL10-2p. This figure shows the promoter activity induced upon addition of galactose.
Figure 4:
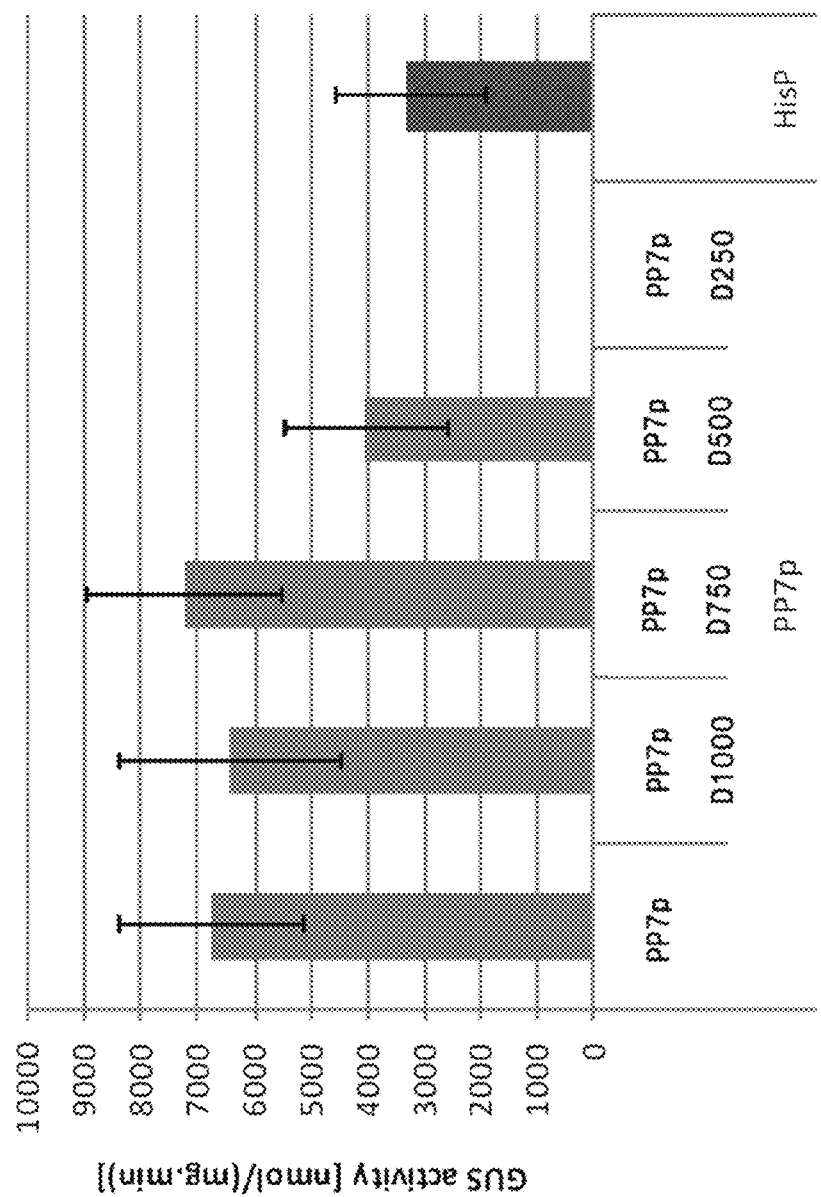
FIG. 4 shows the activity of promoter PP7p and truncated promoters thereof. Culture was conducted in GY medium (10 ml) at 28° C. at 300 rpm for 5 days.
Figure 5:
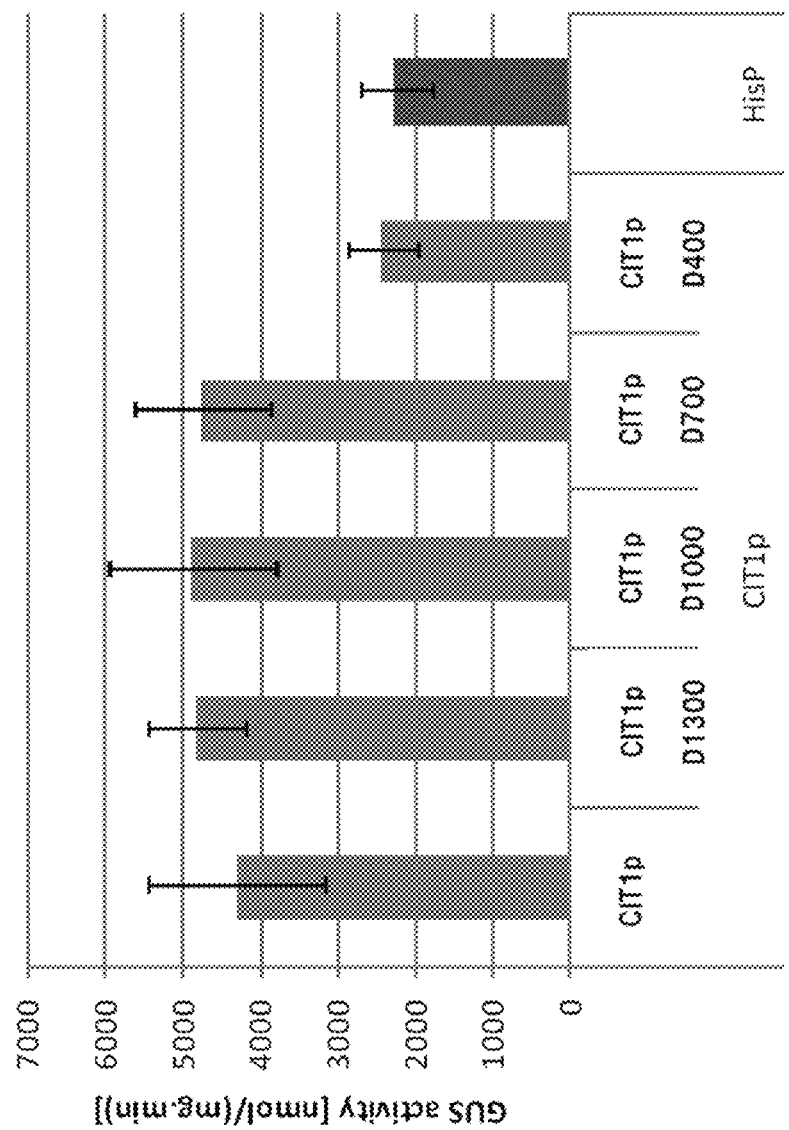
FIG. 5 shows the activity of promoter CIT1p and truncated promoters thereof. Culture was conducted in GY medium (10 ml) at 28° C. at 300 rpm for 3 days.
Figure 6:
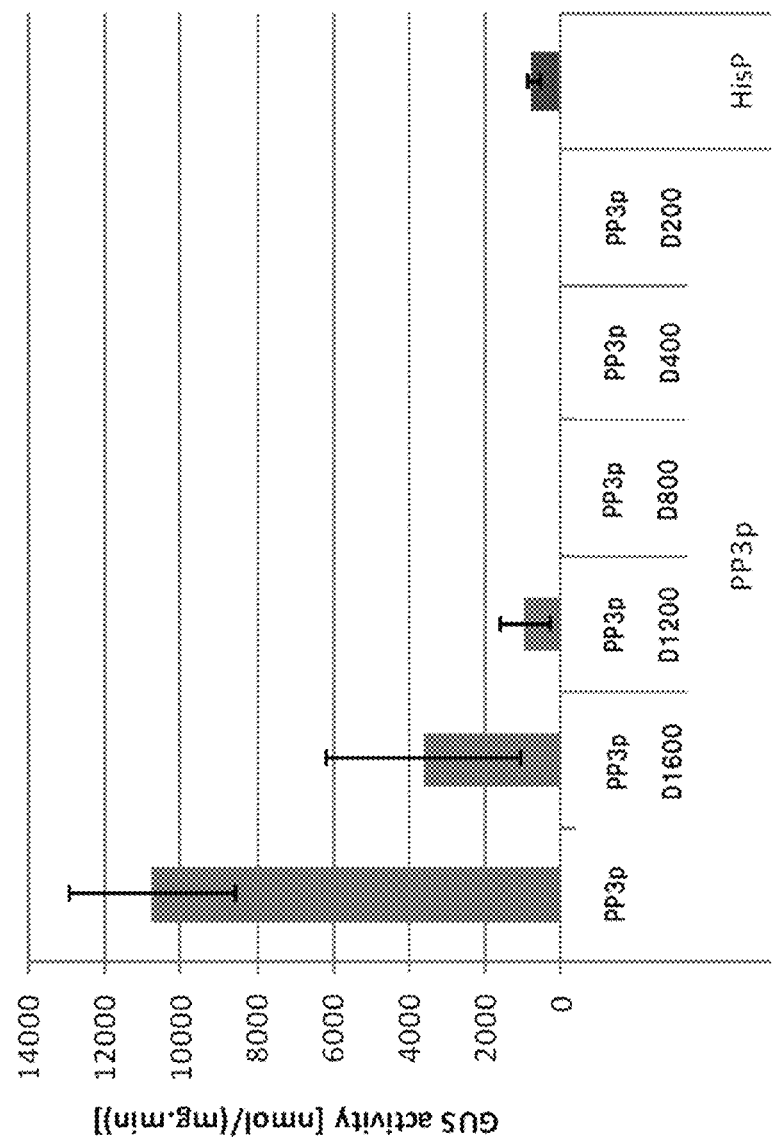
FIG. 6 shows the activity of promoter PP3p and truncated promoters thereof. Culture was conducted in GY medium (10 ml) at 28° C. at 300 rpm for 10 days.
Figure 7:
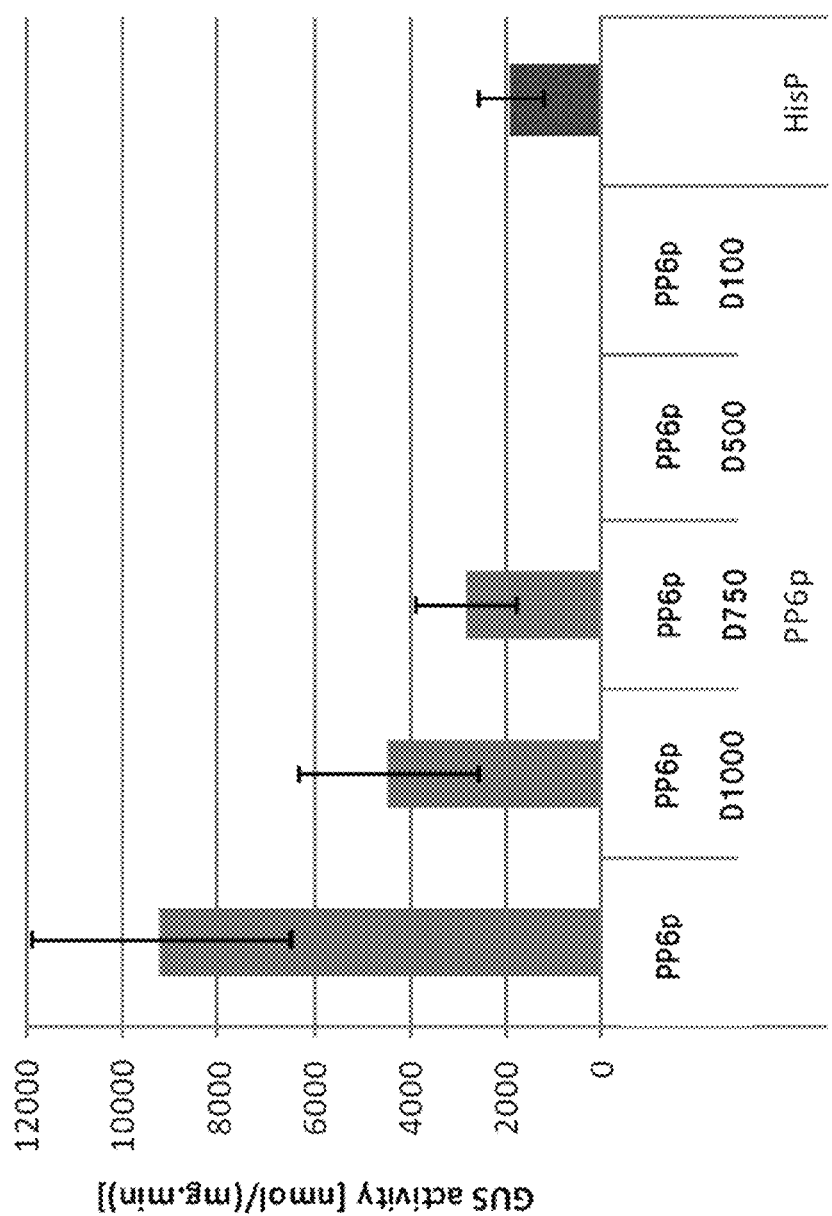
FIG. 7 shows the activity of promoter PP6p and truncated promoters thereof. Culture was conducted in GY medium (10 ml) at 28° C. at 300 rpm for 5 days.
Figure 8:
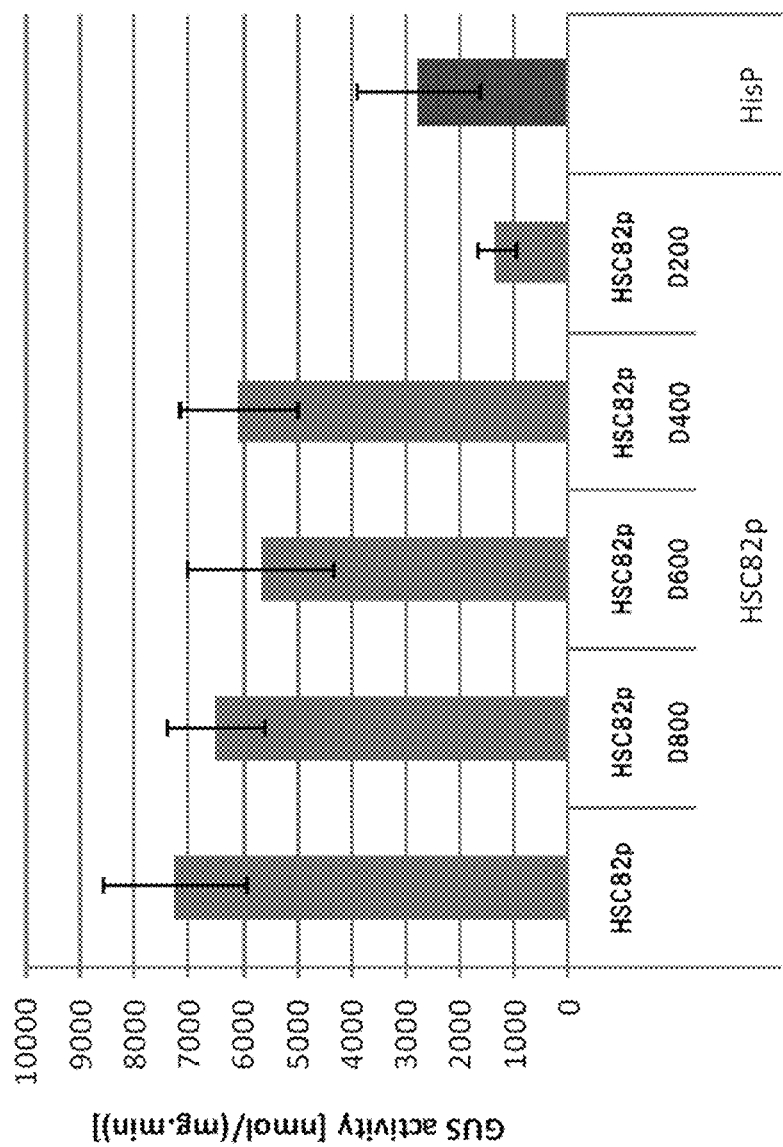
FIG. 8 shows the activity of promoter HSC82p and truncated promoters thereof. Culture was conducted in GY medium (10 ml) at 28° C. at 300 rpm for 5 days.
Figure 9:
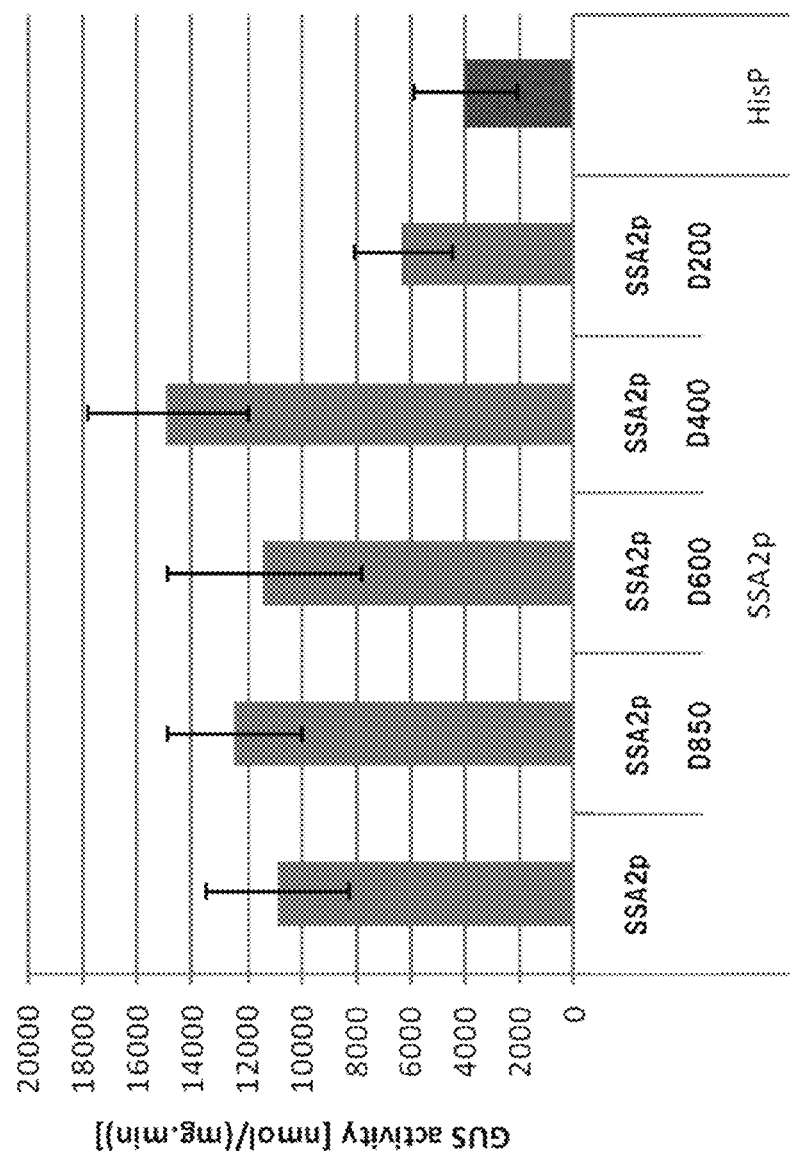
FIG. 9 shows the activity of promoter SSA2p and truncated promoters thereof. Culture was conducted in GY medium (10 ml) at 28° C. at 300 rpm for 5 days.
Figure 10:
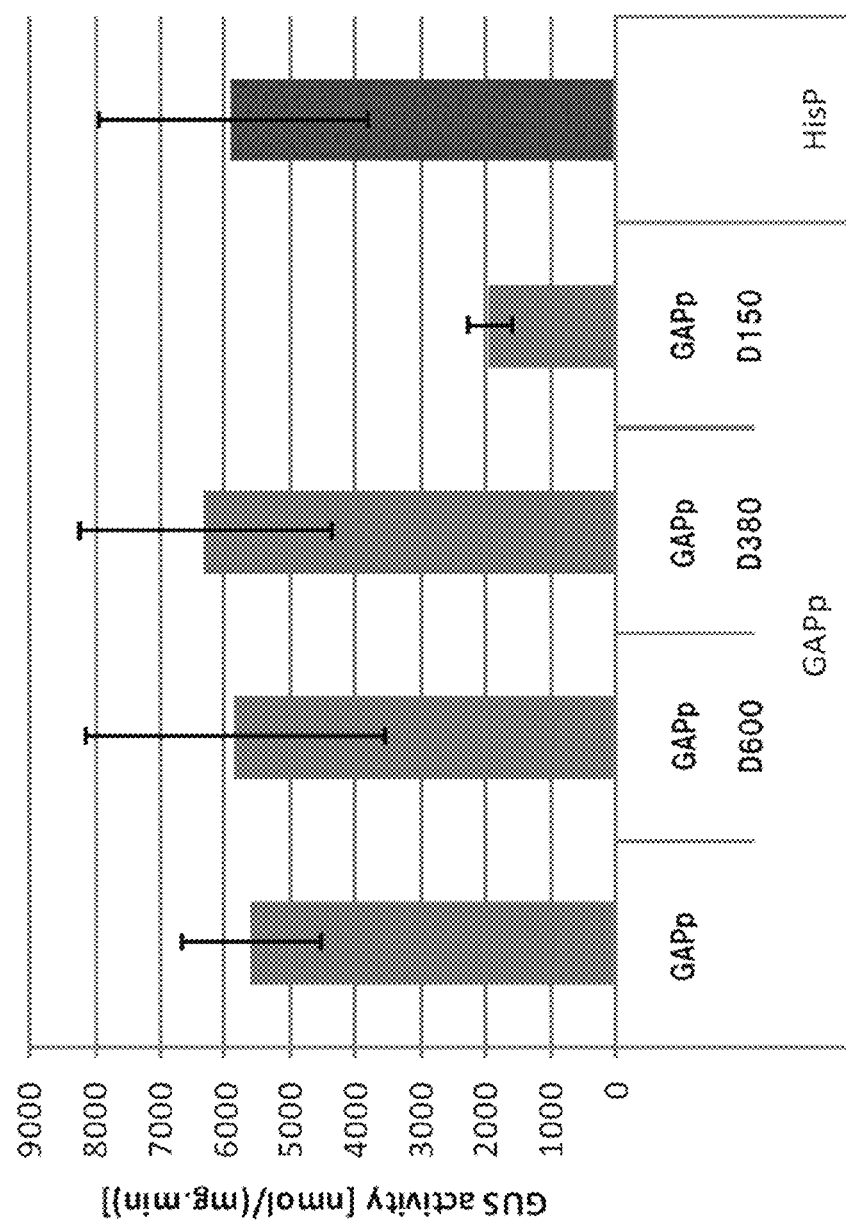
FIG. 10 shows the activity of promoter GAPp and truncated promoters thereof. Culture was conducted in GY medium (10 ml) at 28° C. at 300 rpm for 5 days.

First, stable transformed strains (30 strains) were cultured at 28° C. for 3 days on SC+gal agar medium (SC agar medium containing 2% galactose instead of 2% glucose) and measured for their GUS activity as described above to thereby select 10 strains showing moderate GUS activity. These strains were inoculated into GY liquid medium, and galactose was added thereto at a concentration of 2% on day 4 or 7. Culture conditions were set to 28° C. and 300 rpm. FIG. 3 shows GUS activity measured between 2 and 14 days after initiation of the culture. The promoter GAL10-2p was induced to be expressed upon addition of galactose.

Study on Regions Required for Promoter Activity

To determine a region required for the promoter activity of each promoter, DNA fragments were prepared for each promoter by shortening the upstream region of the promoter, and evaluated for their promoter activity.

To obtain such DNA fragments, the following primers were prepared for each promoter. It should be noted that the underlined parts each represent a restriction enzyme recognition site.

PP7p
Primer for amplification of promoter PP7p-D1000
PP7p D1000 F XbaI
(SEQ ID NO: 49)
AGCA<u>TCTAGA</u>AAAACTATTCAATAATGGGCG Primer for amplification of promoter PP7p-D750
PP7p D750 F XbaI
(SEQ ID NO: 50)
ATTT<u>CTAGA</u>ATGGCGAGACGCAGGGGGTAG Primer for amplification of promoter PP7p-D500
PP7p D500 F XbaI
(SEQ ID NO: 51)
AATA<u>TCTAGA</u>GAGTGGGCACTGAACTAAAAG Primer for amplification of promoter PP7p-D250
PP7p D250 F XbaI
(SEQ ID NO: 52)
AATA<u>TCTAGA</u>GACACTGCATGACGCGAAATC CIT1p
Primer for amplification of promoter CIT1p-D1300
CIT1p D1300 F XbaI
(SEQ ID NO: 53)
AAG<u>TCTAGA</u>TGTCAATCATCTTTGCTGCTG Primer for amplification of promoter CIT1p-D1000
CIT1p D1000 F XbaI
(SEQ ID NO: 54)
TGCG<u>TCTAGA</u>ATTATAATTATAATGAGGAAGTG Primer for amplification of promoter CIT1p-D700
CIT1p D700 F XbaI
(SEQ ID NO: 55)
TTA<u>TCTAGA</u>GGCGAGTGGCGGACTGC Primer for amplification of promoter CIT1p-D400
CIT1p D400 F XbaI
(SEQ ID NO: 56)
TTG<u>TCTAGA</u>CAATTGGCAAGGCTGGGTTG PP3p
Primer for amplification of promoter PP3p-D1600
PP3p D1600 R XbaI
(SEQ ID NO: 57)
AATA<u>TCTAGA</u>GATCCTGGTCGAAAAGACAG Primer for amplification of promoter PP3p-D1200
PP3p D1200 R XbaI
(SEQ ID NO: 58)
AATG<u>TCTAGA</u>TGAGTTTCTGTTTTTTCCTTTTTGC Primer for amplification of promoter PP3p-D800
PP3p D800 R XbaI
(SEQ ID NO: 59)
AATA<u>TCTAGA</u>TGAACAATTCATGCAGCTTCACG Primer for amplification of promoter PP3p-D400
PP3p D400 R XbaI
(SEQ ID NO: 60)
AATA<u>TCTAGA</u>CGTCTAAGCGTTTACGTGCC Primer for amplification of promoter PP3p-D200
PP3p D200 R XbaI
(SEQ ID NO: 61)
AATA<u>TCTAGA</u>CTCGTTTTGATGGAGTTCTC PP2p
Primer for amplification of promoter PP2p-D1200
PP2p D1200 F XbaI
(SEQ ID NO: 62)
ATT<u>TCTAGA</u>TGCATTTACAGGTGAATATTAC Primer for amplification of promoter PP2p-D800
PP2p D800 F XbaI
(SEQ ID NO: 63)
TTA<u>TCTAGA</u>CATAAAAGTGTCTGGAGCG Primer for amplification of promoter PP2p-D400
PP2p D400 F XbaI
(SEQ ID NO: 64)
TTA<u>TCTAGA</u>ACTAAGTGGTGTCTACTTTGG Primer for amplification of promoter PP2p-D200
PP2p D200 F XbaI
(SEQ ID NO: 65)
AAT<u>TCTAGA</u>GGATACTCCATCCCCACCC Primer for amplification of promoter PP6ps
PP6ps-D1000
PP6ps D1000 F XbaI
(SEQ ID NO: 66)
AAT<u>TCTAGA</u>CAGTTACCGTGCGCCCACTG Primer for amplification of promoter PP6ps-D750
PP6ps D750 F XbaI
(SEQ ID NO: 67)
AAT<u>TCTAGA</u>CTTTCACAAATAGGCATCCTATC Primer for amplification of promoter PP6ps-D500
PP6ps D500 F XbaI
(SEQ ID NO: 68)
AAT<u>TCTAGA</u>GGCTTTTTCGTTTATTGGATTG Primer for amplification of promoter PP6ps-D100
PP6ps D100 F XbaI
(SEQ ID NO: 69)
ACG<u>TCTAGA</u>TATCCAATTCTCACCACTTC HSC82p
Primer for amplification of promoter HSC82p-D800
HSC82p D800 F XbaI
(SEQ ID NO: 70)
AAT<u>TCTAGA</u>TTTTACTACCGCATTCCCTTTTC Primer for amplification of promoter HSC82p-D600
HSC82p D600 F XbaI
(SEQ ID NO: 71)
ACG<u>TCTAGA</u>CCTTTTCAGTAAACAATTTC Primer for amplification of promoter HSC82p-D400
HSC82p D400 F XbaI
(SEQ ID NO: 72)
ATT<u>TCTAGA</u>CACAAAGAAGAAGGGTGTGTC Primer for amplification of promoter HSC82p-D200
HSC82p D200 F XbaI
(SEQ ID NO: 73)
ACG<u>TCTAGA</u>ACTGTTTTCTTGAAACTTC SSA2p
Primer for amplification of promoter SSA2p-D850
SSA2p D850 F SpeI
(SEQ ID NO: 74)
AGTA<u>ACTAGT</u>TGACGGCGTGTATATGTCAG Primer for amplification of promoter SSA2p-D600
SSA2p D600 F SpeI
(SEQ ID NO: 75)
AGGT<u>ACTAGT</u>CCATTGTATCGATTTCTGAT Primer for amplification of promoter SSA2p-D400
SSA2p D400 F SpeI
(SEQ ID NO: 76)
AGTA<u>ACTAGT</u>GCTATGCGAACGGTTCATTTTG Primer for amplification of promoter SSA2p-D200
SSA2p D200 F SpeI
(SEQ ID NO: 77)
AGGT<u>ACTAGT</u>TTTTTTCTCTCTGGTGTGAACG GAL10-2p
Primer for amplification of promoter GAL10-2p-D2000
GAL10-2p D2000 F XbaI
(SEQ ID NO: 78)
AAT<u>TCTAGA</u>CGCAGAGTGATGGTCATTACC Primer for amplification of promoter GAL10-2p-D1600
GAL10-2p D1600 F XbaI
(SEQ ID NO: 79)
AAT<u>TCTAGA</u>CTCTATGGCAAGATTACGAG Primer for amplification of promoter GAL10-2p-D1200
GAL10-2p D1200 F XbaI
(SEQ ID NO: 80)
AAT<u>TCTAGA</u>TGCTCGTGAAGAGGGGCAC Primer for amplification of promoter GAL10-2p-D800
GAL10-2p D800 F XbaI
(SEQ ID NO: 81)
ACG<u>TCTAGA</u>CATTTTTTGCCGCCAATTCTG Primer for amplification of promoter GAL10-2p-D400
GAL10-2p D400 F XbaI
(SEQ ID NO: 82)
ATT<u>TCTAGA</u>CCCCCGCCTATTTTTTTTTTC To prepare truncated promoters of each promoter, the previously prepared vector for evaluation of each promoter was used as a template in PCR with the above primers and the reverse primers used in the examples (PP7p R SpeI, CIT1p R SpeI, PP3p R SpeI, PP2p R SpeI, PP6ps R SpeI, HSC82p R SpeI, SSA2p R SpeI, GAL10-2p R XbaI), each corresponding to the 3'-side of each promoter. The resulting DNA fragments were each excised with restriction enzymes XbaI and SpeI or with a restriction enzyme XbaI and then inserted into the vector for promoter evaluation.

In the same manner as described in the section "Transformation of *Mortierella alpina*," *M. alpina* was transformed to select stable transformed strains. These strains were measured for their GUS activity in the same manner as used in the examples. It should be noted that the number of days for culture was set to 3 days (CIT1p), 5 days (PP7p, PP6p, HSC82p, SSA2p, GAPp) or 10 days (PP3p), depending on the properties of each promoter. The results obtained are shown in FIGS. 4 to 10.

Figure 11:
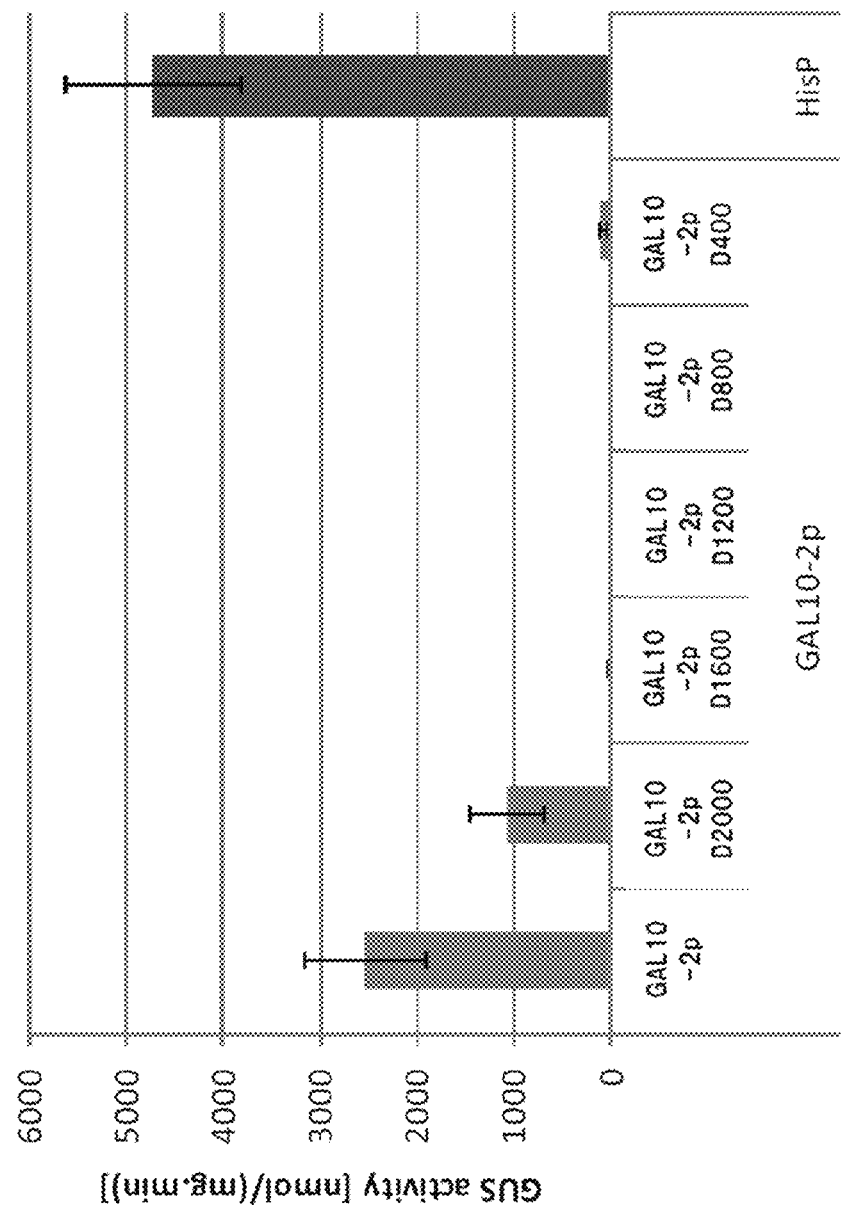
FIG. 11 shows the activity of promoter GAL10-2p and truncated promoters thereof.

In the case of the galactose-inducible promoter, stable transformed strains were pre-cultured at 28° C. for 3 days on SC+gal agar medium (SC agar medium containing 2% galactose instead of 2% glucose) or pre-cultured at 28° C. at 300 rpm for 4 days in SC+raf medium (SC liquid medium containing 2% raffinose instead of 2% glucose), followed by addition of galactose to give a final concentration of 2%. Culture was continued for an additional 1 day, and the cells were measured for their GUS activity. The results obtained are shown in FIG. 11.

As can be seen from FIGS. 4 to 11, the full-length promoters and truncated promoters shown in Table 1 above were each confirmed to show GUS protein activity of 500 nmol/(mg·min) or higher.

INDUSTRIAL APPLICABILITY

The present invention enables the high expression of target genes in lipid-producing fungi and thereby allows efficient synthesis and collection of target proteins, lipids and fatty acids.

Sequence Listing Free Text

SEQ ID NOs: 31 to 82: synthetic DNAs

Sequence Listing

---

The invention claimed is:

1. A vector comprising a polynucleotide selected from:
   (a) a polynucleotide which contains any one nucleotide sequence selected from SEQ ID NOs: 22 to 26; or
   (b) a polynucleotide which has a nucleotide sequence sharing an identity of 90% or more with any one nucleotide sequence selected from SEQ ID NOs: 22 to 26 and which shows promoter activity in cells of microorganisms belonging to the genus *Mortierella*.

2. The vector according to claim 1, wherein the promoter activity is confirmed as β-D-glucuronidase (GUS) protein activity of at least 500 nmol/(mg·min) upon expression of GUS reporter gene in cells of microorganisms belonging to the genus *Mortierella*.

3. The vector according to claim 1, which comprises any one nucleotide sequence selected from SEQ ID NOs: 22 to 26.

4. The vector according to claim 1, which is DNA.

5. A microbial transformant transformed with the vector according to claim 1.

6. The transformant according to claim 5, wherein the transformant is a lipid-producing fungus.

7. The transformant according to claim 6, wherein the lipid-producing fungus is *Mortierella alpina*.

* * * * *

SEQUENCE LISTING

<160> NUMBER OF SEQ ID NOS: 82

<210> SEQ ID NO 1
<211> LENGTH: 1341
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 1

```
tgaccgtgcg cttttttgaga cggttgatag gtacaacacg acgctaacat gaggctagtg       60
cggcaacttt tttacgccct cggtaacaaa aaaatcgtct cattcatatg tcagaatcgt      120
gctctctttg tcaccaagga gacgcctctc cctcccgtca gggccttgtc aaaactaccg      180
cccaaaacac aaagttggca tccgatgaaa gtcgagtgag cgtctatttt ttttatttta      240
gatcgcttct aatgcagatc tgaaaactat tcaataatgg gcgcccactc aaacacgcgg      300
ccagggcgga aaaggagtg ggagttgtga aaaatgagag acaattgttg attctttggg      360
atactgatgt ccatttggtg ctgctcgtcc tcctttgggt caaaagaagg cgcagccatg      420
cacggccctt tcttattgac aaagtcccta actgcttacc aaagtctttt ctagctcttc      480
atcttttatt ttttataaaa aaaggtccga caccctatg ttcgaaggtg ctagacggat      540
caagaatatc atcgagatgg cgagacgcag ggggtagagc ggacatagtg acagtttcaa      600
ggtcagcata tagaaaggcg gtcaaggcaa gctggtgcct gagatccgtt tgccagacaa      660
agagaagatg ttcgtgtatg gtcacgatcc cgaaaagaat aattcaaaac agctctaggt      720
gaaggctata ttcgtcctca gatctttcta cacagaaagg gaggtacact tgggccactt      780
gatgcaactt tctccgacgt tgactgggtc tgaaaaacaa agaacctcag tttcggtccg      840
agagtgggca ctgaactaaa aaggaaaccc attttcgagg cattcggtcg ggttagagtt      900
caattcttat tttatggtcc tcccgtcgga tgtgtcagtg tttgggcggc caagacgaca      960
acagtgaggg gatcgagcac acctgctgag gggggcggtg tgctctcaaa tagggaaaat     1020
atccaatcta ggccgttccc ttattgaccg gatagttttc tttcctttgt ttgctgactg     1080
agtttcgggt agacactgca tgacgcgaaa tccatcgaag gagtttgaaa atatcgacgt     1140
ggaggcaaaa tgcttacctc cccaatactc gcaatgctgc cccatgactt tgcgcgtgca     1200
acagaaccga aaaaaggtat aagaacctgg tttccgtcct ccaccatttg tcttttctct     1260
```

```
cttctaacct tcattccaat ctacaacaca agaacaaccc acaaataacc caactcaatc    1320
ccacctttca acaaatatac g                                              1341

<210> SEQ ID NO 2
<211> LENGTH: 1079
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 2
aaaactattc aataatgggc gcccactcaa acacgcggcc agggcggaaa aaggagtggg      60
agttgtgaaa aatgagagac aattgttgat tctttgggat actgatgtcc atttggtgct    120
gctcgtcctc ctttgggtca aagaaggcg cagccatgca cggcccttc ttattgacaa      180 agtccctaac tgcttaccaa agtctttct agctcttcat ctttattt ttataaaaaa       240 aggtccgaca cccctatgtt cgaaggtgct agacggatca agaatatcat cgagatggcg    300
agacgcaggg ggtagagcgg acatagtgac agtttcaagg tcagcatata gaaaggcgt    360 caaggcaagc tggtgcctga gatccgtttg ccagacaaag agaagatgtt cgtgtatggt    420
cacgatcccg aaagaataa ttcaaaacag ctctaggtga aggctatatt cgtcctcaga    480
tctttctaca cagaaaggga ggtacacttg gccacttga tgcaacttc tccgacgttg     540 actgggtctg aaaaacaaag aacctcagtt tcggtccgag agtgggcact gaactaaaaa    600
ggaaacccat tttcgaggca ttcggtcggg ttagagttca attcttattt tatggtcctc    660
ccgtcggatg tgtcagtgtt tgggcggcca agacgacaac agtgagggga tcgagcacac    720
ctgctgaggg gggcggtgtg ctctcaaata gggaaaatat ccaatctagg ccgttccctt    780
attgaccgga tagtttttctt tcctttgttt gctgactgag tttcgggtag acactgcatg    840
acgcgaaatc catcgaagga gtttgaaaat atcgacgtgg aggcaaaatg cttacctccc    900
caatactcgc aatgctgccc catgactttg cgcgtgcaac agaaccgaaa aaaggtataa    960
gaacctggtt tccgtcctcc accatttgtc ttttctctct tctaaccttc attccaatct   1020
acaacacaag aacaacccac aaataaccca actcaatccc cctttcaac aaatatacg     1079

<210> SEQ ID NO 3
<211> LENGTH: 785
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 3
atggcgagac gcaggggggta gagcggacat agtgacagtt tcaaggtcag catatagaaa      60
ggcggtcaag gcaagctggt gcctgagatc cgtttgccag acaaagagaa gatgttcgtg    120
tatggtcacg atcccgaaaa gaataattca aaacagctct aggtgaaggc tatattcgtc    180
ctcagatctt tctacacaga aagggaggta cacttgggcc acttgatgca actttctccg    240
acgttgactg ggtctgaaaa acaaagaacc tcagtttcgg tccgagagtg ggcactgaac    300
taaaaaggaa acccattttc gaggcattcg gtcgggttag agttcaattc ttattttatg    360
gtcctcccgt cggatgtgtc agtgtttggg cggccaagac gacaacagtg aggggatcga    420
gcacacctgc tgagggggggc ggtgtgctct caaatagggga aaatatccaa tctaggccgt    480
```

```
tcccttattg accggatagt tttctttcct ttgtttgctg actgagtttc gggtagacac        540
tgcatgacgc gaaatccatc gaaggagttt gaaaatatcg acgtggaggc aaaatgctta        600
cctccccaat actcgcaatg ctgccccatg actttgcgcg tgcaacagaa ccgaaaaaag        660
gtataagaac ctggtttccg tcctccacca tttgtctttt ctctcttcta accttcattc        720
caatctacaa cacaagaaca acccacaaat aacccaactc aatcccacct ttcaacaaat        780
atacg                                                                   785

<210> SEQ ID NO 4
<211> LENGTH: 500
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 4
gagtgggcac tgaactaaaa aggaaaccca ttttcgaggc attcggtcgg gttagagttc         60
aattcttatt ttatggtcct cccgtcggat gtgtcagtgt ttgggcggcc aagacgacaa        120
cagtgagggg atcgagcaca cctgctgagg ggggcggtgt gctctcaaat agggaaaata        180
tccaatctag gccgttccct tattgaccgg atagttttct ttcctttgtt tgctgactga        240
gtttcgggta gacactgcat gacgcgaaat ccatcgaagg agtttgaaaa tatcgacgtg        300
gaggcaaaat gcttacctcc ccaatactcg caatgctgcc ccatgacttt gcgcgtgcaa        360
cagaaccgaa aaaggtata agaacctggt tccgtcctc caccatttgt cttttctctc        420
ttctaacctt cattccaatc tacaacacaa gaacaaccca caataaccc aactcaatcc        480 caccttttcaa caaatatacg                                                  500

<210> SEQ ID NO 5
<211> LENGTH: 1593
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 5
attttctaga cacctcaaaa acgtgccttg ttgttcctgt taggctgaag ctctgctgta         60
cacacgaggt tgaagccggg taggttttag ttgggtgcga gtgccgtgat ctgggccgag        120
agtttgtcac tgaatcagct aaatagcgga aagtgtgatg cacaatcagg aacgttggtg        180
gcacgatgca acgtcgaggt atgggcggcc gtgctcgctg gtgcttcctt taagatcgag        240
gacatagtgc agtacgtctt tcttgagctg aagtttgtgt gtctcgtctc tctctttctc        300
tctcgcatcc tgttaatgtg tcgtccaaag tgtcaatcat ctttgctgct gatctctggg        360 cacttttcttc cttagtgtgc cgtatatgga caattgtggg gttccctgct cttaaggcaa        420
gggcagatag cgtgggtagg ttggaaactc aagcgaaata acacagtgaa gccacgcttg        480
atgagaggaa acatgttgca caaaagtgta aaaaaaaaaa ttagagactg ccagagggag        540
gtgaggcaag ttgtgacaaa tcctatttta tgtattgtca agcctgaggt cgacggccat        600
cctttactcg cttcagcttt cggatcacat attataatta taatgaggaa gtgttggttt        660
gggagacagg agtggaggtt ttgataaata aaaaagtgg cagatcaagg agaatgtggc        720
gatccatgaa caaaaaagat ggcggttttt tcttgatcga attcggtctc ccaccagatc        780
atatgccgat ggtagagttg atctgccggt ggttatacca cggacctggt ggtgtataga        840
```

| | | | |
|---|---|---|---|
| ttatcaagct | catttccaag tgcagcgtag | aatacaaaga cgctagatga | tccaagcgac | 900 |
| gatgggtacg | gcgatgatga | tgccaacgat | ggcgagtggc | ggactgctcc | gtcccgagcg | 960 |
| ggatgatgat | tgtgccgatg | tggaaaccac | ctgcgacggt | ggtctacaat | actgttgctg | 1020 |
| ttataaataa | cggcgttaga | gtactactat | agtgtagact | gatgggttct | ctgtgaaagg | 1080 |
| aaagaggagt | cggtattttg | aatactagcc | cgagggggtt | tttttgatgg | gttgtgcctg | 1140 |
| aatagttgtt | gcgctgttct | ttttgatct | aaagagttga | ggagcagccc | gtacgtcact | 1200 |
| ttatcgattc | aatcgccggt | ggcctgtatt | caattggcaa | ggctgggttg | ctgcccggtg | 1260 |
| cttatctcca | gaggacaggg | cctggcgagg | aaggggagat | gctcagactg | ctcagacagg | 1320 |
| cacacagaca | atttcaaagt | ccacatgcaa | agaaaacaaa | aaaaaaaaaa | aatgtaattc | 1380 |
| ccttccccct | gcaacatgtc | gtatgtgcgg | gtggaaggaa | acgtttctgt | tctcatcaca | 1440 |
| tccgatcaca | agtgtctctg | tctccgcccg | acgcttttt | ttattcttct | ttttttctgt | 1500 |
| cttttctctt | tcttttttc | tcttctcttt | tctttcttct | ttctctcctc | atcttcttcc | 1560 |
| actcactccc | ctctctccat | acacatatcc | gcc | | | 1593 |

<210> SEQ ID NO 6
<211> LENGTH: 1263
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 6

| | | | | | |
|---|---|---|---|---|---|
| tgtcaatcat | ctttgctgct | gatctctggg | cactttcttc | cttagtgtgc | cgtatatgga | 60 |
| caattgtggg | gttccctgct | cttaaggcaa | gggcagatag | cgtgggtagg | ttggaaactc | 120 |
| aagcgaaata | acacagtgaa | gccacgcttg | atgagaggaa | acatgttgca | caaaagtgta | 180 |
| aaaaaaaaaa | ttagagactg | ccagagggag | gtgaggcaag | ttgtgacaaa | tcctatttta | 240 |
| tgtattgtca | agcctgaggt | cgacggccat | cctttactcg | cttcagcttt | cggatcacat | 300 |
| attataatta | taatgaggaa | gtgttggttt | gggagacagg | agtggaggtt | ttgataaata | 360 |
| aaaaaagtgg | cagatcaagg | agaatgtggc | gatccatgaa | caaaaaagat | ggcggttttt | 420 |
| tcttgatcga | attcggtctc | ccaccagatc | atatgccgat | ggtagagttg | atctgccggt | 480 |
| ggttatacca | cggacctggt | ggtgtataga | ttatcaagct | catttccaag | tgcagcgtag | 540 |
| aatacaaaga | cgctagatga | tccaagcgac | gatgggtacg | gcgatgatga | tgccaacgat | 600 |
| ggcgagtggc | ggactgctcc | gtcccgagcg | ggatgatgat | tgtgccgatg | tggaaaccac | 660 |
| ctgcgacggt | ggtctacaat | actgttgctg | ttataaataa | cggcgttaga | gtactactat | 720 |
| agtgtagact | gatgggttct | ctgtgaaagg | aaagaggagt | cggtattttg | aatactagcc | 780 |
| cgagggggtt | tttttgatgg | gttgtgcctg | aatagttgtt | gcgctgttct | ttttgatct | 840 |
| aaagagttga | ggagcagccc | gtacgtcact | ttatcgattc | aatcgccggt | ggcctgtatt | 900 |
| caattggcaa | ggctgggttg | ctgcccggtg | cttatctcca | gaggacaggg | cctggcgagg | 960 |
| aaggggagat | gctcagactg | ctcagacagg | cacacagaca | atttcaaagt | ccacatgcaa | 1020 |
| agaaaacaaa | aaaaaaaaaa | aatgtaattc | ccttccccct | gcaacatgtc | gtatgtgcgg | 1080 |
| gtggaaggaa | acgtttctgt | tctcatcaca | tccgatcaca | agtgtctctg | tctccgcccg | 1140 |
| acgcttttt | ttattcttct | ttttttctgt | cttttctctt | tcttttttc | tcttctcttt | 1200 |
| tctttcttct | ttctctcctc | atcttcttcc | actcactccc | ctctctccat | acacatatcc | 1260 |

```
gcc                                                                   1263

<210> SEQ ID NO 7
<211> LENGTH: 963
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 7
attataatta taatgaggaa gtgttggttt gggagacagg agtggaggtt ttgataaata      60
aaaaaagtgg cagatcaagg agaatgtggc gatccatgaa caaaaaagat ggcggttttt     120
tcttgatcga attcggtctc ccaccagatc atatgccgat ggtagagttg atctgccggt     180
ggttatacca cggacctggt ggtgtataga ttatcaagct catttccaag tgcagcgtag     240
aatacaaaga cgctagatga tccaagcgac gatgggtacg gcgatgatga tgccaacgat     300
ggcgagtggc ggactgctcc gtcccgagcg ggatgatgat tgtgccgatg tggaaaccac     360
ctgcgacggt ggtctacaat actgttgctg ttataaataa cggcgttaga gtactactat     420
agtgtagact gatgggttct ctgtgaaagg aaagaggagt cggtattttg aatactagcc     480
cgagggggtt ttttgatgg gttgtgcctg aatagttgtt gcgctgttct ttttgatct      540 aaagagttga ggagcagccc gtacgtcact ttatcgattc aatcgccggt ggcctgtatt     600
caattggcaa ggctgggttg ctcccggtg cttatctcca aggacagggg cctggcgagg      660
aaggggagat gctcagactg ctcagacagg cacacagaca atttcaaagt ccacatgcaa     720
agaaaacaaa aaaaaaaaa aatgtaattc ccttcccct gcaacatgtc gtatgtgcgg       780
gtggaaggaa acgtttctgt tctcatcaca tccgatcaca agtgtctctg tctccgcccg     840
acgctttttt ttattcttct tttttctgt cttttctctt ttcttttttc tcttctcttt      900
tctttcttct ttctctcctc atcttcttcc actcactccc ctctctccat acacatatcc     960
gcc                                                                   963

<210> SEQ ID NO 8
<211> LENGTH: 663
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 8
ggcgagtggc ggactgctcc gtcccgagcg ggatgatgat tgtgccgatg tggaaaccac      60
ctgcgacggt ggtctacaat actgttgctg ttataaataa cggcgttaga gtactactat     120
agtgtagact gatgggttct ctgtgaaagg aaagaggagt cggtattttg aatactagcc     180
cgagggggtt ttttgatgg gttgtgcctg aatagttgtt gcgctgttct ttttgatct      240 aaagagttga ggagcagccc gtacgtcact ttatcgattc aatcgccggt ggcctgtatt     300
caattggcaa ggctgggttg ctcccggtg cttatctcca aggacagggg cctggcgagg      360
aaggggagat gctcagactg ctcagacagg cacacagaca atttcaaagt ccacatgcaa     420
agaaaacaaa aaaaaaaaa aatgtaattc ccttcccct gcaacatgtc gtatgtgcgg       480
gtggaaggaa acgtttctgt tctcatcaca tccgatcaca agtgtctctg tctccgcccg     540
acgctttttt ttattcttct tttttctgt cttttctctt ttcttttttc tcttctcttt      600
```

```
tctttcttct ttctctcctc atcttcttcc actcactccc ctctctccat acacatatcc    660
gcc                                                                  663

<210> SEQ ID NO 9
<211> LENGTH: 363
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 9
caattggcaa ggctgggttg ctgcccggtg cttatctcca gaggacaggg cctggcgagg    60
aaggggagat gctcagactg ctcagacagg cacacagaca atttcaaagt ccacatgcaa    120
agaaaacaaa aaaaaaaaaa aatgtaattc ccttcccct gcaacatgtc gtatgtgcgg     180
gtggaaggaa acgtttctgt tctcatcaca tccgatcaca agtgtctctg tctccgcccg    240 acgcttttt ttattcttct ttttttctgt cttttctctt ttcttttttc tcttctcttt    300
tctttcttct ttctctcctc atcttcttcc actcactccc ctctctccat acacatatcc    360
gcc                                                                  363

<210> SEQ ID NO 10
<211> LENGTH: 2294
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 10
tcgtgttatc ttgcgctgca tgtttcgttg ccgagtcgtt attaatctat gggcgttcta    60
ctctaggttt tgcgtacgtt accaatgcat ttggacctcc tgagacttta ctgggagact    120
acagggccaa gactttgctg gaccgtgtcg tctatgctag aaaggaggag ctcggattgc    180
tcccaatgaa ggaggccaac agcgaggcca agagtgaggc caagaactaa aggcgttcca    240
ttaaaactat gctgctttc gtgctccctt tttttttttt tttttttttt ttacttttac     300
ttttgcctga cgtgaactgc acaatgctgc aaaatcatga aggagtcaag acaatgacgg    360
gagagagtaa acaccatccc caccactctg tagaggaaca tcacgcggtt ccgttttgtg    420
cactcctccc tttgagacaa tccttgcagt ctgatgggcg cttttcttct cacggttgtc    480
gctgaaattt tgttgcctca caggcgcgta tgatatcaat tactgcacgc cgttgcttgg    540
tgttcttggc tatctctttt ccagagctga tgctggtcgg cgtatctcta tgatgcaacc    600
ttccctgcct tctctgattc ctgtagtctg cagcctctag ttcgatcctg gtcgaaaaag    660
acaggcgcaa tgtccctcat cccggaactt tcggcaaagc ccagttcttc gccatcttta    720
aaacaacagc acctacgccc tcctcgcagt actttgatcc ctccccattc aaaagagaca    780
ttttagtaga aaacggttga aaggaaaaa gatttctgta gaacgtaaag catgagaaaa     840
aagtaatgct ctccctgtag atgcatcctc ctgtttctgg ctttactttg aaccgacttg    900
ctccaaacga tcatgcccaa attaataaag gacatcgacc aacggaggct ttagcaggac    960
agtgcgcctc tatgtacatg tacactacaa ggatgatcat gcattgtatg ccgattttgg    1020
ctgcattgcg atcgcactgg cgagacagag aaaggggggtg tgtatttcaa gaacgagaag    1080 gcgaggggg gactgagttt ctgttttttc ctttttgcat aactgtcgac aagagacggt     1140
gtatgaagtg aagaggaaac acaaggggtg catggacgtt gaggaacagt aacattcgtg    1200
```

```
atgggtctag gtgattgggg gcagtgtgcc ttctaatgca caccagaacc aagccattga    1260
gtatcgctat ggcttgccta tgatagcatg gaccgcagaa agaaaccttt ttgctgctaa    1320
ctgggaccag aatagcgcgg tctgtcatca actaacgtta tggtcctctg tagcctggga    1380
agaacggact gagggtgttt cgttgaatgt caaggggcat gcgccaaaaa acacatgca    1440 cgggggaaca tgcggaagcg cgattgtgat tttcattctt ttttcggtct gtgtgaacaa    1500
ttcatgcagc ttcacgagca tgttcgatgg aaaggaacag tgctctattt ttcagagtag    1560
tctagcatag gatttgagag ccgagttgct tgcttacgat gtcactgtgt ggagtgttgg    1620
agcgcaatcc ctgcttttc aattatcttt ggcatacgtg gaagacctgg ccgttcagta    1680
cacgcccgcg aaatgtcatt caatgccctg tccaatcttg accataggct tagacacggt    1740
cccccaagct tcctccaaac aatcgcgttt atttatatac ttcatcatgc atatgagatc    1800
acacctgtta aactagatcg caaccgtaca atagtgtgct ctcagttgac caggggcagc    1860
tacaaaacgg tccggctgga gtgttttttt tgacgtctaa gcgtttacgt gccattgact    1920
acttcgagct ttcaaacgct tggcccaggg aggtctcgac agctaagaga acgtacgcga    1980
ccttctcttt ggtccattga gcaaagtttc ccacacacat agtagttgga tatgcctgtt    2040
caccatcgtt gggcattgca ccaaaaggca tcccgctgaa agctgtcatg aaactcgttt    2100
tgatggagtt ctcaatcaca tcacctcaca tcattttgca ccctgcccgg gtggaaaaaa    2160
tactcccagg cctcagctcg cgcctcctca cgatcgcttt tcgtataaaa accatcctcc    2220
ttcgcgctcc ttttcatcca tattctcact tttgtctcta tccctcagc taaaaccaac    2280 acctctaaat catc                                                      2294

<210> SEQ ID NO 11
<211> LENGTH: 1651
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 11
gatcctggtc gaaaagaca ggcgcaatgt ccctcatccc ggaactttcg gcaaagccca      60
gttcttcgcc atctttaaaa caacagcacc tacgccctcc tcgcagtact ttgatccctc    120
cccattcaaa agagacattt tagtagaaaa cggttgagaa ggaaaaagat ttctgtagaa    180
cgtaaagcat gagaaaaaag taatgctctc cctgtagatg catcctcctg tttctggctt    240
tactttgaac cgacttgctc caaacgatca tgcccaaatt aataaaggac atcgaccaac    300
ggaggcttta gcaggacagt gcgcctctat gtacatgtac actacaagga tgatcatgca    360
ttgtatgccg attttggctg cattgcgatc gcactggcga gacagagaaa gggggtgtgt    420
atttcaagaa cgagaaggcg agggggggac tgagtttctg tttttttcctt tttgcataac    480 tgtcgacaag agacggtgta tgaagtgaag aggaaacaca aggggtgcat ggacgttgag    540
gaacagtaac attcgtgatg ggtctaggtg attgggggca gtgtgccttc taatgcacac    600
cagaaccaag ccattgagta tcgctatggc ttgcctatga tagcatggac cgcagaaaga    660 aaccttttg ctgctaactg ggaccagaat agcgcggtct gtcatcaact aacgttatgg    720
tcctctgtag cctgggaaga acggactgag ggtgttcgt tgaatgtcaa ggggcatgcg    780
ccaaaaaaca catatgacgg gggaacatgc ggaagcgcga ttgtgatttt cattctttt    840 tcggtctgtg tgaacaattc atgcagcttc acgagcatgt tcgatggaaa ggaacagtgc    900
```

```
tctatttttc agagtagtct agcataggat ttgagagccg agttgcttgc ttacgatgtc      960
actgtgtgga gtgttggagc gcaatccctg cttttcaat tatctttggc atacgtggaa     1020
gacctggccg ttcagtacac gcccgcgaaa tgtcattcaa tgccctgtcc aatcttgacc    1080
ataggcttag acacggtccc ccaagcttcc tccaaacaat cgcgtttatt tatatacttc    1140
atcatgcata tgagatcaca cctgttaaac tagatcgcaa ccgtacaata gtgtgctctc    1200
agttgaccag gggcagctac aaaacggtcc ggctggagtg ttttttttga cgtctaagcg    1260
tttacgtgcc attgactact tcgagctttc aaacgcttgg cccagggagg tctcgacagc    1320
taagagaacg tacgcgacct tctctttggt ccattgagca agtttccca cacacatagt     1380
agttggatat gcctgttcac catcgttggg cattgcacca aaaggcatcc cgctgaaagc    1440
tgtcatgaaa ctcgttttga tggagttctc aatcacatca cctcacatca ttttgcaccc   1500
tgcccgggtg aaaaaatac tcccaggcct cagctcgcgc ctcctcacga tcgcttttcg    1560
tataaaaacc atcctccttc gcgctccttt tcatccatat tctcactttt gtctctatcc    1620
cctcagctaa aaccaacacc tctaaatcat c                                  1651
```

<210> SEQ ID NO 12  
<211> LENGTH: 1201  
<212> TYPE: DNA  
<213> ORGANISM: Artificial Sequence  
<220> FEATURE:  
<223> OTHER INFORMATION: Description of Artificial Sequence: Synthetic polynucleotide

<400> SEQUENCE: 12

```
tgagtttctg tttttccctt tttgcataac tgtcgacaag agacggtgta tgaagtgaag      60
aggaaacaca aggggtgcat ggacgttgag gaacagtaac attcgtgatg ggtctaggtg     120
attggggca gtgtgccttc taatgcacac cagaaccaag ccattgagta tcgctatggc     180
ttgcctatga tagcatggac cgcagaaaga aaccttttg ctgctaactg ggaccagaat      240
agcgcggtct gtcatcaact aacgttatgg tcctctgtag cctgggaaga acggactgag    300
ggtgtttcgt tgaatgtcaa ggggcatgcg ccaaaaaaca catatgacgg gggaacatgc    360
ggaagcgcga ttgtgatttt cattcttttt tcggtctgtg tgaacaattc atgcagcttc    420
acgagcatgt tcgatggaaa ggaacagtgc tctatttttc agagtagtct agcataggat    480
ttgagagccg agttgcttgc ttacgatgtc actgtgtgga gtgttggagc gcaatccctg    540
cttttcaat tatctttggc atacgtggaa gacctggccg ttcagtacac gcccgcgaaa     600
tgtcattcaa tgccctgtcc aatcttgacc ataggcttag acacggtccc ccaagcttcc    660
tccaaacaat cgcgtttatt tatatacttc atcatgcata tgagatcaca cctgttaaac    720
tagatcgcaa ccgtacaata gtgtgctctc agttgaccag gggcagctac aaaacggtcc    780
ggctggagtg ttttttttga cgtctaagcg tttacgtgcc attgactact tcgagctttc    840
aaacgcttgg cccagggagg tctcgacagc taagagaacg tacgcgacct tctctttggt    900
ccattgagca agtttccca cacacatagt agttggatat gcctgttcac catcgttggg     960
cattgcacca aaaggcatcc cgctgaaagc tgtcatgaaa ctcgttttga tggagttctc   1020
aatcacatca cctcacatca ttttgcaccc tgcccgggtg aaaaaatac tcccaggcct    1080
cagctcgcgc ctcctcacga tcgcttttcg tataaaaacc atcctccttc gcgctccttt   1140
tcatccatat tctcactttt gtctctatcc cctcagctaa aaccaacacc tctaaatcat   1200
c                                                                   1201
```

<210> SEQ ID NO 13
<211> LENGTH: 1609
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 13

```
gactgtaaag acggagggga gcaccaggat tagtaacgta cactctctat ctcaataaga      60
tttaatatga attttctcag aggacactgc tcttcctacg cgatgattca actgctgccg     120
ttttctccca tatccataca gcgaggttta gcaggtctat ggtcgctctc agacagcgat     180
tcgcgcccaa aacagcattc tcggcaatga tttgaggctt cgaaactgtt cgcggaaata     240
ccacagaggt gtgcattcac tgatacatgt acataggttg atggtacaat gacaagaaca     300
caggatagta acatcgatcg gaggcaactt tggagctacc ggatggccgg gcatgagaaa     360
atctcgcatc tgtaatacat aaacgtctcc gtatctttat agggctcaat tgcatttaca     420
ggtgaatatt acaactaggc actcttcttc aaaagaaaca ggatttggta gtgattggtg     480
gactaatgga cgaaagtgac attctgttac catgaagtcc aaactgggga tctcgtttga     540
ccggcattcg cacctggtga atctaggatg cttggatgca ggagccgccg ctttccttgc     600
ttcctccttt gagtgacatg aattcagaag tactgttttt ctggagctca ttctgcacat     660
ttggggggttg ggtgcttaca gtactgggga tgacgttcac ctacttgcct ctctgttcaa     720
ttcacctcga gagaaatgac caaagtatct gcgtctgagc cagcgcctgg atatatggcg     780
ttataaattc ataaaagtgt ctggagcgat cctccagcag gcgtgtttgt ggactgcacg     840
caataccgcg tcgccaaatt cgccatcgac gcgaaagagt gcgattctcg cgctcgaacg     900
caagttgtgc ctgtgtggtg taacgtttga ggaaaatatc ctgcatgaat gggacatgcg     960
cactgaggag ttcctctcac tgggattgat acagaagaag gtgttactca tcccctagga    1020
gctcgtttct atgattaggc aatttcgact ccagcaccgg tatgttcgta ccaaagggcc    1080
atagctccaa ggataaggaa aaatagacct cacctcatgc tcagctgaac aagttgtggt    1140
gaagtacgtg cctcggggat tcaaccatcc atatccaatc atttcataat gcatggctgc    1200
atctctacac actaagtggt gtctactttg gagggtacca aaactttgtt cccaatgcat    1260
tactttgtaa atgctttgta aataacgcga gacgcgtcga tattgtggag ttgtgtgagg    1320
ggtgggaaca aaattgtacc gcaaccccac cacaatgcgc gcatgaatct gctcaaccat    1380
gtccttgaca gaagaggcag gtccaatgga tactccatcc ccaccccgcg cccttttcaa    1440
ccccgagtct tctgtaattc ctaatatagc ctttcaaagc gtgtcagggc actgcattct    1500
ccttcaagca tcagcttaca ttgccggaag tgttataaaa aggcgcctcc ctttgttttc    1560
tgatcctcat cctcccccac ttttctaaa ccactaccca ctatccaca              1609
```

<210> SEQ ID NO 14
<211> LENGTH: 1519
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 14

```
ctggcaatag ttagtgcacg cttgtacgaa tatgctgtgc gctgtacaaa ccaactttac      60
```

```
acacacgaga tcaaaatctg aatagtgacc agactggcaa aaagcaggtg caattgccaa    120
aagttgacgc tatatttaga agtatgtcga ttctctctat ctgcggcttt gcatatttcc    180
cgcctcctct tcctttccca ccttgtcccc agtattcaac tgaggccatt actttgtata    240
gtctagtaca tgtacaagtg aaattgagca tggaggcgaa ggccttggag caacagccgt    300
gcccacttct ttggtcctcc aattgcatgc aagcacggtg agggctgaca attaatgaat    360
gaaagattca atagtcgacg cgtttccagt ggacagtccc acagctctct caataccagt    420
ccccgaacgc cctcgcccat tccatcctcc ccccgccttg tgtccactgg atgctatgca    480
gatgggagca ctctgaggca tgattccaat cttttcaggc agttaccgtg cgcccactgt    540
ttattgctca cagtcgacaa cgtactccct acctccccat ctcatcccct cccacacttg    600
attagggcgc cacacagtgt atatataaaa atggtgagcg tggctgggtg tcgaagaaac    660
gtatgggagg gatcttacta aaaaaaagcc gtccttggga caccgccccc attctctctg    720
cagtgactgc agcactgaac gcatcgagtg ctaccgaccc cgctccggac tttcacaaat    780
aggcatccta tcccgattct attttctgac catcctgccg acatgagttg gctgcagttt    840
gccccataat gtctgtgtgt ttaatgtcgc atgagaaaga atatgaaaga aagaaaaaag    900
agtgagaacg aaaggaaaaa gactgggatg taacgagtac aaagagaaac agccgctcat    960
gatacacaaa aatgacCCCg tttggaaaat gaagtgggcg taacggttaa cattccgttg   1020 gcttttttcgt ttattggatt gcgaattgtt ggacccatga atgcatgcct cggaaaacaa   1080
atgggtgtcc attcgtacaa gtgttaagat aggttcaacc ttatcatcca acggtcgaca   1140
cgggaaatgg cagaccgcgc cttgaacgta acggccaaac gaaaaattag aaggcactat   1200
gttcatctat tgttcaatgc tgtgtctcaa agaagtccct cgctcattat tcagtccctc   1260
gccccaagta ccatagacga caagtgtcca aaaaaaaaaa aaaaaaaaaa aaacgcaatc   1320
taaaccaggt catggacacc gttacgctcg gtcaggggcc ttgccttagc ctctgtcgcg   1380
ttcgtataaa gcctgcggtt tcagcgaaac atttcccttt cttctttatc caattctcac   1440
cacttctttt cagaacccac ctataaacct acccaccCCa ctccaaccaa cccccacct    1500 tctcaaacaa acctccatc                                                1519
```

<210> SEQ ID NO 15
<211> LENGTH: 1000
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 15

```
cagttaccgt gcgcccactg tttattgctc acagtcgaca acgtactccc tacctcccca     60
tctcatcccc tcccacactt gattagggcg ccacacagtg tatatataaa aatggtgagc    120
gtggctgggt gtcgaagaaa cgtatgggag ggatcttact aaaaaaaagc cgtccttggg    180
acaccgcccc cattctctct gcagtgactg cagcactgaa cgcatcgagt gctaccgacc    240
ccgctccgga ctttcacaaa taggcatcct atcccgattc tattttctga ccatcctgcc    300
gacatgagtt ggctgcagtt tgccccataa tgtctgtgtg tttaatgtcg catgagaaag    360
aatatgaaag aaagaaaaaa gagtgagaac gaaaggaaaa agactgggat gtaacgagta    420
caaagagaaa cagccgctca tgatacacaa aaatgacccc gtttggaaaa tgaagtgggc    480
gtaacggtta acattccgtt ggcttttttcg tttattggat tgcgaattgt tggacccatg    540
```

```
aatgcatgcc tcggaaaaca aatgggtgtc cattcgtaca agtgttaaga taggttcaac      600
cttatcatcc aacggtcgac acgggaaatg gcagaccgcg ccttgaacgt aacggccaaa      660
cgaaaaatta gaaggcacta tgttcatcta ttgttcaatg ctgtgtctca aagaagtccc      720
tcgctcatta ttcagtccct cgccccaagt accatagacg acaagtgtcc aaaaaaaaaa      780
aaaaaaaaaa aaaacgcaat ctaaaccagg tcatggacac cgttacgctc ggtcaggggc      840
cttgccttag cctctgtcgc gttcgtataa agcctgcggt ttcagcgaaa catttccctt      900
tcttctttat ccaattctca ccacttcttt tcagaaccca cctataaacc tacccacccc      960
actccaacca accccccacc ttctcaaaca aacctccatc                          1000

<210> SEQ ID NO 16
<211> LENGTH: 750
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 16
ctttcacaaa taggcatcct atcccgattc tatttcctga ccatcctgcc gacatgagtt       60
ggctgcagtt tgccccataa tgtctgtgtg tttaatgtcg catgagaaag aatatgaaag      120
aaagaaaaaa gagtgagaac gaaaggaaaa agactgggat gtaacgagta caaagagaaa      180
cagccgctca tgatacacaa aaatgacccc gtttggaaaa tgaagtgggc gtaacggtta      240
acattccgtt ggcttttttcg tttattggat tgcgaattgt tggacccatg aatgcatgcc      300
tcggaaaaca aatgggtgtc cattcgtaca agtgttaaga taggttcaac cttatcatcc      360
aacggtcgac acgggaaatg gcagaccgcg ccttgaacgt aacggccaaa cgaaaaatta      420
gaaggcacta tgttcatcta ttgttcaatg ctgtgtctca aagaagtccc tcgctcatta      480
ttcagtccct cgccccaagt accatagacg acaagtgtcc aaaaaaaaaa aaaaaaaaaa      540
aaaacgcaat ctaaaccagg tcatggacac cgttacgctc ggtcaggggc cttgccttag      600
cctctgtcgc gttcgtataa agcctgcggt ttcagcgaaa catttccctt tcttctttat      660
ccaattctca ccacttcttt tcagaaccca cctataaacc tacccacccc actccaacca      720
accccccacc ttctcaaaca aacctccatc                                      750

<210> SEQ ID NO 17
<211> LENGTH: 1000
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 17
gagctcaaga tgaaggtgct caacgttgtc tatgtgacag atcgtcagga gcgtgtggag       60
gagtgcgtac tctgccggat gggcgtcaat gtcgaaggac tgcacgagca cccaccaagc      120
aggttctgag ctcaatattt ttttttcttt cttagacctc ttctttattg catcctatca      180
gccaacaaat tcccttcttt ttttactacc gcattccctt ttccttattg tgtgtttgtt      240
cttccatgcc tatcatcttg ggacgaacaa acagactatg gcatagggga acggatatga      300
cagaaggcgc agttgaaaca gcatacaatc ctgggcaaac agtatttttcc ggccttctta      360 ttctcctacc ttgctcgaat gagctcttgt atatagaata tccttttcag taaacaattt      420
cttaacctca tatgaatatt cgcagctgtg ccttcgctat gatcaggttg ccttgtcaag      480
```

```
gatcaagttg gcgtcgtcct tttgggttgg atcaggcagc atgccttgcc tgccaacgaa    540
agctggttgg cgagacaaga ggtagcaaca gcatttgcct ccgtatttcg aaaaatattt    600
cacaaagaag aagggtgtgt cggctcaggc ccttacttcg cctgcgctca aaaaacagac    660
agctgcggga tggatatcag cattttgaa tgaaggggc agaagtggaa ggccgcatct      720
gtacgtcttc gccacggtag ttctactgga aaatcgcttg aagacgcatg agggatttag    780
aggctttaaa tccagccatg actgttttct tgaaacttct tttgcaaaga aaatagagct    840
gcagcgtgca ggcacaaaga gagtcggtgc tccctgctca cggaatatgc tggaaggttt    900
tctttgacga ggcggcacat atatatgggg cccgcgcctt cgttctttt cttctgtttc     960 ctcatcttct cttcactcct tcccgcaaac cacacacacc                         1000
```

<210> SEQ ID NO 18
<211> LENGTH: 800
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 18

```
ttttactacc gcattccctt ttccttattg tgtgtttgtt cttccatgcc tatcatcttg     60
ggacgaacaa acagactatg gcataggga acgatatga cagaaggcgc agttgaaaca      120
gcatacaatc ctgggcaaac agtatttcc ggccttctta ttctcctacc ttgctcgaat    180
gagctcttgt atatagaata tccttttcag taaacaattt cttaacctca tatgaatatt    240
cgcagctgtg ccttcgctat gatcaggttg ccttgtcaag gatcaagttg gcgtcgtcct    300
tttgggttgg atcaggcagc atgccttgcc tgccaacgaa agctggttgg cgagacaaga    360
ggtagcaaca gcatttgcct ccgtatttcg aaaaatattt cacaaagaag aagggtgtgt    420
cggctcaggc ccttacttcg cctgcgctca aaaaacagac agctgcggga tggatatcag    480 cattttgaa tgaaggggc agaagtggaa ggccgcatct gtacgtcttc gccacggtag      540
ttctactgga aaatcgcttg aagacgcatg agggatttag aggctttaaa tccagccatg    600
actgttttct tgaaacttct tttgcaaaga aaatagagct gcagcgtgca ggcacaaaga    660
gagtcggtgc tccctgctca cggaatatgc tggaaggttt tctttgacga ggcggcacat    720
atatatgggg cccgcgcctt cgttctttt cttctgtttc ctcatcttct cttcactcct     780
tcccgcaaac cacacacacc                                               800
```

<210> SEQ ID NO 19
<211> LENGTH: 599
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 19

```
ccttttcagt aaacaatttc ttaacctcat atgaatattc gcagctgtgc cttcgctatg     60
atcaggttgc cttgtcaagg atcaagttgg cgtcgtcctt ttgggttgga tcaggcagca    120
tgccttgcct gccaacgaaa gctggttggc gagacaagag gtagcaacag catttgcctc    180
cgtatttcga aaaatatttc acaaagaaga agggtgtgtc ggctcaggcc cttacttcgc    240
ctgcgctcaa aaaacagaca gctgcgggat ggatatcagc attttgaat gaaggggca      300
```

```
gaagtggaag gccgcatctg tacgtcttcg ccacggtagt tctactggaa aatcgcttga    360
agacgcatga gggatttaga ggctttaaat ccagccatga ctgttttctt gaaacttctt    420
ttgcaaagaa aatagagctg cagcgtgcag gcacaaagag agtcggtgct ccctgctcac    480
ggaatatgct ggaaggtttt ctttgacgag gcggcacata tatatggggc ccgcgccttc    540 gttcttttc ttctgtttcc tcatcttctc ttcactcctt cccgcaaacc acacacacc     599
```

<210> SEQ ID NO 20
<211> LENGTH: 400
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 20

```
cacaaagaag aagggtgtgt cggctcaggc ccttacttcg cctgcgctca aaaacagac      60 agctgcggga tggatatcag cattttttgaa tgaaaggggc agaagtggaa ggccgcatct   120
gtacgtcttc gccacggtag ttctactgga aaatcgcttg aagacgcatg agggatttag   180
aggctttaaa tccagccatg actgttttct gaaacttct tttgcaaaga aaatagagct    240
gcagcgtgca ggcacaaaga gagtcggtgc tccctgctca cggaatatgc tggaaggttt   300
tctttgacga ggcggcacat atatatgggg cccgcgcctt cgttcttttt cttctgtttc   360
ctcatcttct cttcactcct tcccgcaaac cacacacacc                         400
```

<210> SEQ ID NO 21
<211> LENGTH: 200
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 21

```
actgttttct gaaacttct tttgcaaaga aaatagagct gcagcgtgca ggcacaaaga      60
gagtcggtgc tccctgctca cggaatatgc tggaaggttt tctttgacga ggcggcacat   120
atatatgggg cccgcgcctt cgttcttttt cttctgtttc ctcatcttct cttcactcct   180
tcccgcaaac cacacacacc                                                200
```

<210> SEQ ID NO 22
<211> LENGTH: 999
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 22

```
aaagtgctgc ttcggaaccg ttagacaatg ttccgtgccc gacaagagca agtcttcttg      60
attgggaaaa ctttacaggg gagcagatcg aggctctcgg tgccgaagtg ctgatcctct    120
cagatttggt aaggaccatt tttcttcgtt ttttttgac ggcgtgtata tgtcagtcca     180
tgtttccagc cgtgctatgc ccacgcatta atcaaattgc cgtaaaagac ctatgatccg    240
acaaacatcg tgccacttgt tactgttctg aaggcaatgc ttgttaaagg cgtcaccgcg    300
tacatgtcct cagctattcg aaatccgcaa acatttatcg acttttttgc ccgtatcagt    360
aagtggttcc ccttgtgccg ttgcaccaac tgtgcttgac ccattgtatc gatttctgat    420
```

```
atagtatctt gaatgacgtt caaacagggc aagagtgcgt cggcgtagag gttcaggaaa      480
tagatctgag tagcactgag cacctgttct tctttgatga ggagacagtg cagaccgtga      540
aggtgtttcg cctttattat ccgtaaagaa tgataagcaa aaaaaaaaaa aaataaacgc      600
gctatgcgaa cggttcattt tgcgatgtgt cttaaaaaca agttccaggc atggaaaaaa      660
cgatgattgg gtccggggcc gcggagcaca gcctcgcaga atcgtgaggg tgctggaggg      720
tgctggagca tggtggaacc tcgattagct catttccacg tacggctgta cgtgccagac      780
caaaactctt ttttgcattt ttttttctct ctggtgtgaa cgcattggcg agggcggagg      840
cacagagaag gcgatagaac gcggtggaac gaaaaggaac attgagcacg cagtggtgga      900
tcgcatctgc catataaaat acacgccccg cctttttgctt tccgtttttcc tcttttttttc  960 ttcactcatc cctccaacac tcacactcac atctacatc                            999
```

```
<210> SEQ ID NO 23
<211> LENGTH: 843
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 23
tgacggcgtg tatatgtcag tccatgtttc cagccgtgct atgcccacgc attaatcaaa       60
ttgccgtaaa agacctatga tccgacaaac atcgtgccac ttgttactgt tctgaaggca     120
atgcttgtta aaggcgtcac cgcgtacatg tcctcagcta ttcgaaatcc gcaaacattt     180
atcgactttt ttgcccgtat cagtaagtgg ttccccttgt gccgttgcac caactgtgct     240
tgacccattg tatcgatttc tgatatagta tcttgaatga cgttcaaaca gggcaagagt     300
gcgtcggcgt agaggttcag gaaatagatc tgagtagcac tgagcacctg ttcttctttg     360
atgaggagac agtgcagacc gtgaaggtgt ttcgccttta ttatccgtaa agaatgataa     420
gcaaaaaaaa aaaaaaataa acgcgctatg cgaacggttc attttgcgat gtgtcttaaa     480
aacaagttcc aggcatggaa aaacgatga ttgggtccgg ggccgcggag cacagcctcg     540
cagaatcgtg agggtgctgg agggtgctgg agcatggtgg aacctcgatt agctcatttc     600
cacgtacggc tgtacgtgcc agaccaaaac tcttttttgc attttttttt ctctctggtg     660
tgaacgcatt ggcgagggcg gaggcacaga gaaggcgata gaacgcggtg gaacgaaaag     720
gaacattgag cacgcagtgg tggatcgcat ctgccatata aaatacacgc ccgcctttt     780 gctttccgtt ttcctctttt tttcttcact catccctcca acactcacac tcacatctac     840
atc                                                                    843
```

```
<210> SEQ ID NO 24
<211> LENGTH: 599
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 24
ccattgtatc gatttctgat atagtatctt gaatgacgtt caaacagggc aagagtgcgt       60
cggcgtagag gttcaggaaa tagatctgag tagcactgag cacctgttct tctttgatga     120
ggagacagtg cagaccgtga aggtgtttcg cctttattat ccgtaaagaa tgataagcaa     180
aaaaaaaaaa aaataaacgc gctatgcgaa cggttcattt tgcgatgtgt cttaaaaaca     240
```

```
agttccaggc atggaaaaaa cgatgattgg gtccggggcc gcggagcaca gcctcgcaga      300
atcgtgaggg tgctggaggg tgctggagca tggtggaacc tcgattagct catttccacg      360
tacggctgta cgtgccagac caaaactctt ttttgcattt ttttttctct ctggtgtgaa      420
cgcattggcg agggcggagg cacagagaag gcgatagaac gcggtggaac gaaaaggaac      480
attgagcacg cagtggtgga tcgcatctgc catataaaat acacgccccg ccttttgctt      540
tccgttttcc tcttttttc ttcactcatc cctccaacac tcacactcac atctacatc      599

<210> SEQ ID NO 25
<211> LENGTH: 399
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 25
gctatgcgaa cggttcattt tgcgatgtgt cttaaaaaca agttccaggc atggaaaaaa       60
cgatgattgg gtccggggcc gcggagcaca gcctcgcaga atcgtgaggg tgctggaggg      120
tgctggagca tggtggaacc tcgattagct catttccacg tacggctgta cgtgccagac      180
caaaactctt ttttgcattt ttttttctct ctggtgtgaa cgcattggcg agggcggagg      240
cacagagaag gcgatagaac gcggtggaac gaaaaggaac attgagcacg cagtggtgga      300
tcgcatctgc catataaaat acacgccccg ccttttgctt tccgttttcc tcttttttc      360 ttcactcatc cctccaacac tcacactcac atctacatc                            399

<210> SEQ ID NO 26
<211> LENGTH: 199
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 26
ttttttctct ctggtgtgaa cgcattggcg agggcggagg cacagagaag gcgatagaac       60
gcggtggaac gaaaaggaac attgagcacg cagtggtgga tcgcatctgc catataaaat      120
acacgccccg ccttttgctt tccgttttcc tcttttttc ttcactcatc cctccaacac      180
tcacactcac atctacatc                                                 199

<210> SEQ ID NO 27
<211> LENGTH: 2331
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 27
ggttccgaga ggtggatttg gtggaatgga tgcaaagtga ttcacaggaa acgattgtcg       60
gatccgattt caccttggcc aaatgatgag cggtcacatc gggcgccatt tcatttcata      120
ttgatatcca tcacagggaa acgcgcaaga tcgaacttaa ggcggtcgat gaggctggct      180
ggaagaggca ttgtccgtgt cggcgtagag agtacggaga ggaagagacg ctgtagtggt      240
ggatgttgtc gcgagctgga gagagccatg cggcggagct cactcggcgt gggatcaact      300
gtggggacgc agaataccag cgcaccgacc acgcagagtg atggtcatta ccaacaaaac      360
```

```
ataaacaaag gggcaaagga cctcactctt tgcatgcccc catcctccat cttcgcgctc    420
acatccgtcc ccctatttc gtgaaggcag gcactcattg taaagtggaa ggatgatgta    480
cgacgattgc ctgatatgag ctcagtatgc atcaagcaag ctagcttcgg acagacatca    540
acaaagacc atactgaggc gggtcttgtg ccacttccaa caacatattt taccgacagc    600
gtggtacttt tagcttctgg gcgtaaagac aaacagaaag tatcgttcac ttccccaaac    660
cttctcatgc ctattgataa ttgttggttt agtgtctggc aaagcacaat ggaaaatgat    720
agttggcgaa actctatggc aagattacga gattacgctt atcgattggc gtcgagcgtg    780
tctctccgcc gtctatgacc tcgggcctag taaccaccgt gacagagatg gaatagttga    840
aggctatgga agcacccgtg agagaagatg gggttgtaca agaacggata aaccgaaaac    900
cataacgctg cgcgtgtggg gcaagtaatg cggatgatga cagcctgtgc ctgatgttca    960
cgttaaaaac ctcgtctctc tcacgcatca gggcgcgccc aaccacagaa acacgaagag   1020
gatcatgggg gatgagagac gagggcgagt gtgcaggaaa gcgtgtcgct agcatgacac   1080
aaagcagctg ctactagcct gcttagagcg caggccattg aacacaatac tgaactctag   1140
tccaggcggt ggtttcgagg agcagaaact agtatgctcg tgaagagggg cacgtcgggg   1200
gtggacggag ggaacaagtt gaggctatat aatgtcctct aaactcaccg tcgtcccgtc   1260
tttccttctc ttttctttct gtcttcttgc ctcttgcttt caatggtcct ccgcaacaat   1320
caacactaag ctccttacac cacttggtac agaccgctcc tctcctctta cccactcgcc   1380
atctgctcac tacctcaaga tgcccatgct gacaccgtcc tcaagcccct tagcaggtat   1440
cgcaccctct tctccacttg atgctctatc tcacctattc atatgggca ctcccattct    1500
gtgtcgatac gatgcacatt ttttcttttt tcatttttg ccgccaattc tgtttgtgag   1560
tggccaggac tccgcgagat gtatatttt tttttcattc ttctaggggt agtcaatctc   1620
gctgggactg aattaaactg tgttttgtg caccctgagt taagcgttca tttctctgtt   1680
caccatatca tcatcccgca atgagctctc ggtctgcgcc catgcgtgtg ctgggatcgg   1740
ctccgcacag gcttcctttc gcatactcat gcacagacac atgcacacat gcacacatgc   1800
tcagagtgac agtgcggata tatcgtggtg ctgtgcatgc cttgcgtgga ggcaggctgc   1860
tgtggtgtct cccggcctgg ggcattcgac gaggtgccga gtgccgaaga acaggaccta   1920
tccccctgtg gccccccgcct attttttttt tctttttttc attctttcat tcttttttgtt  1980
tttatatatc tgccccttca ctcttttatc ttttcactcg tccataccctc acttcccgct   2040
gctccattcc aattacattc caactccatt ccaattacat tccaactcca ttccaacagc   2100
attcctagca ttctcattct ctccattcaa tctccttccc tctgacccga gctcacttt    2160
tgccacctgc tgcaccccctt cgcccaccac cctttgctc accgtgtgtt acctcccccg   2220
gtgctccttt ttttccattt ttgccgccct ttttcttatt tcttgctagg cccaccctct   2280
gtcactgcaa ttccgcccat tcacccgacc acctcgtcct ttcaggagcc a           2331
```

<210> SEQ ID NO 28
<211> LENGTH: 2000
<212> TYPE: DNA
<213> ORGANISM: Artificial Sequence
<220> FEATURE:
<223> OTHER INFORMATION: Description of Artificial Sequence: Synthetic
  polynucleotide

<400> SEQUENCE: 28

```
cgcagagtga tggtcattac caacaaaaca taaacaaagg ggcaaaggac ctcactcttt     60
```

```
gcatgccccc atcctccatc ttcgcgctca catccgtccc cctatttcg tgaaggcagg    120 cactcattgt aaagtggaag gatgatgtac gacgattgcc tgatatgagc tcagtatgca    180
tcaagcaagc tagcttcgga cagacatcaa caaaagacca tactgaggcg ggtcttgtgc    240
cacttccaac aacatatttt accgacacgcg tggtactttt agcttctggg cgtaaagaca    300
aacagaaagt atcgttcact tccccaaacc ttctcatgcc tattgataat tgttggttta    360
gtgtctggca aagcacaatg gaaaatgata gttggcgaaa ctctatggca agattacgag    420
attacgctta tcgattggcg tcgagcgtgt ctctccgccg tctatgaccc cgggcctagt    480
aaccaccgtg acagagatgg aatagttgaa ggctatggaa gcacccgtga gagaagatgg    540
ggttgtacaa gaacggataa accgaaaacc ataacgctgc gcgtgtgggg caagtaatgc    600
ggatgatgac agcctgtgcc tgatgttcac gttaaaaacc tcgtctctct cacgcatcag    660
ggcgcgccca accacagaaa cacgaagagg atcatggggg atgagagacg agggcgagtg    720
tgcaggaaag cgtgtcgcta gcatgacaca aagcagctgc tactagcctg cttagagcgc    780
aggccattga acacaatact gaactctagt ccaggcggtg gtttcgagga cagaaacta    840 gtatgctcgt gaagaggggc acgtcggggg tggacggagg gaacaagttg aggctatata    900
atgtcctcta aactcaccgt cgtcccgtct ttccttctct tttctttctg tcttcttgcc    960
tcttgctttc aatggtcctc cgcaacaatc aacactaagc tccttacacc acttggtaca   1020
gaccgctcct ctcctcttac ccactcgcca tctgctcact acctcaagat gcccatgctg   1080
acaccgtcct caagccccctt agcaggtatc gcaccctctt ctccacttga tgctctatct   1140
cacctattca tatgggcac tcccattctg tgtcgatacg atgcacattt tttcttttt   1200 cattttttgc cgccaattct gtttgtgagt ggccaggact ccgcgagatg tatatttttt   1260
ttttcattct tctaggggta gtcaatctcg ctgggactga attaaactgt gttttgtgc   1320 accctgagtt aagcgttcat ttctctgttc accatatcat catcccgcaa tgagctctcg   1380
gtctgcgccc atgcgtgtgc tgggatcggc tccgcacagg cttccttttcg catactcatg   1440 cacagacaca tgcacacatg cacacatgct cagagtgaca gtgcggatat atcgtggtgc   1500
tgtgcatgcc ttgcgtggag gcaggctgct gtggtgtctc ccggcctggg gcattcgacg   1560
aggtgccgag tgccgaagaa caggacctat cccctgtggc ccccgcccta tttttttttt   1620 cttttttca ttctttcatt cttttgttt ttatatatct gccccttcac tctttatct   1680 tttcactcgt ccatacctca cttcccgctg ctccattcca attacattcc aactccattc   1740
caattacatt ccaactccat tccaacagca ttcctagcat tctcattctc tccattcaat   1800
ctccttccct ctgacccgag ctcacttttt gccacctgct gcacccctc gcccaccacc   1860 cttttgctca ccgtgtgtta cctcccccgg tgctcctttt tttccatttt tgccgcccttt  1920 tttcttattt cttgctaggc ccaccctctg tcactgcaat tccgcccatt cacccgacca   1980
cctcgtcctt tcaggagcca                                              2000
```

<210> SEQ ID NO 29
<211> LENGTH: 1812
<212> TYPE: DNA
<213> ORGANISM: Escherichia coli
<220> FEATURE:
<221> NAME/KEY: CDS
<222> LOCATION: (1)..(1809)

<400> SEQUENCE: 29

```
atg tta cgt cct gta gaa acc cca acc cgt gaa atc aaa aaa ctc gac    48
```

```
                Met Leu Arg Pro Val Glu Thr Pro Thr Arg Glu Ile Lys Lys Leu Asp
                1               5                   10                  15 ggc ctg tgg gca ttc agt ctg gat cgc gaa aac tgt gga att gat cag            96
Gly Leu Trp Ala Phe Ser Leu Asp Arg Glu Asn Cys Gly Ile Asp Gln
            20                  25                  30 cgt tgg tgg gaa agc gcg tta caa gaa agc cgg gca att gct gtg cca           144
Arg Trp Trp Glu Ser Ala Leu Gln Glu Ser Arg Ala Ile Ala Val Pro
        35                  40                  45 ggc agt ttt aac gat cag ttc gcc gat gca gat att cgt aat tat gcg           192
Gly Ser Phe Asn Asp Gln Phe Ala Asp Ala Asp Ile Arg Asn Tyr Ala
    50                  55                  60 ggc aac gtc tgg tat cag cgc gaa gtc ttt ata ccg aaa ggt tgg gca           240
Gly Asn Val Trp Tyr Gln Arg Glu Val Phe Ile Pro Lys Gly Trp Ala
65                  70                  75                  80 ggc cag cgt atc gtg ctg cgt ttc gat gcg gtc act cat tac ggc aaa           288
Gly Gln Arg Ile Val Leu Arg Phe Asp Ala Val Thr His Tyr Gly Lys
                85                  90                  95 gtg tgg gtc aat aat cag gaa gtg atg gag cat cag ggc ggc tat acg           336
Val Trp Val Asn Asn Gln Glu Val Met Glu His Gln Gly Gly Tyr Thr
            100                 105                 110 cca ttt gaa gcc gat gtc acg ccg tat gtt att gcc ggg aaa agt gta           384
Pro Phe Glu Ala Asp Val Thr Pro Tyr Val Ile Ala Gly Lys Ser Val
        115                 120                 125 cgt atc acc gtt tgt gtg aac aac gaa ctg aac tgg cag act atc ccg           432
Arg Ile Thr Val Cys Val Asn Asn Glu Leu Asn Trp Gln Thr Ile Pro
    130                 135                 140 ccg gga atg gtg att acc gac gaa aac ggc aag aaa aag cag tct tac           480
Pro Gly Met Val Ile Thr Asp Glu Asn Gly Lys Lys Lys Gln Ser Tyr
145                 150                 155                 160 ttc cat gat ttc ttt aac tat gcc gga atc cat cgc agc gta atg ctc           528
Phe His Asp Phe Phe Asn Tyr Ala Gly Ile His Arg Ser Val Met Leu
                165                 170                 175 tac acc acg ccg aac acc tgg gtg gac gat atc acc gtg gtg acg cat           576
Tyr Thr Thr Pro Asn Thr Trp Val Asp Asp Ile Thr Val Val Thr His
            180                 185                 190 gtc gcg caa gac tgt aac cac gcg tct gtt gac tgg cag gtg gtg gcc           624
Val Ala Gln Asp Cys Asn His Ala Ser Val Asp Trp Gln Val Val Ala
        195                 200                 205 aat ggt gat gtc agc gtt gaa ctg cgt gat gcg gat caa cag gtg gtt           672
Asn Gly Asp Val Ser Val Glu Leu Arg Asp Ala Asp Gln Gln Val Val
    210                 215                 220 gca act gga caa ggc act agc ggg act ttg caa gtg gtg aat ccg cac           720
Ala Thr Gly Gln Gly Thr Ser Gly Thr Leu Gln Val Val Asn Pro His
225                 230                 235                 240 ctc tgg caa ccg ggt gaa ggt tat ctc tat gaa ctg tgc gtc aca gcc           768
Leu Trp Gln Pro Gly Glu Gly Tyr Leu Tyr Glu Leu Cys Val Thr Ala
                245                 250                 255 aaa agc cag aca gag tgt gat atc tac ccg ctt cgc gtc ggc atc cgg           816
Lys Ser Gln Thr Glu Cys Asp Ile Tyr Pro Leu Arg Val Gly Ile Arg
            260                 265                 270 tca gtg gca gtg aag ggc gaa cag ttc ctg att aac cac aaa ccg ttc           864
Ser Val Ala Val Lys Gly Glu Gln Phe Leu Ile Asn His Lys Pro Phe
        275                 280                 285 tac ttt act ggc ttt ggt cgt cat gaa gat gcg gac ttg cgt ggc aaa           912
Tyr Phe Thr Gly Phe Gly Arg His Glu Asp Ala Asp Leu Arg Gly Lys
    290                 295                 300 gga ttc gat aac gtg ctg atg gtg cac gac cac gca tta atg gac tgg           960
Gly Phe Asp Asn Val Leu Met Val His Asp His Ala Leu Met Asp Trp
305                 310                 315                 320
```

```
att ggg gcc aac tcc tac cgt acc tcg cat tac cct tac gct gaa gag        1008
Ile Gly Ala Asn Ser Tyr Arg Thr Ser His Tyr Pro Tyr Ala Glu Glu
                325                 330                 335 atg ctc gac tgg gca gat gaa cat ggc atc gtg gtg att gat gaa act        1056
Met Leu Asp Trp Ala Asp Glu His Gly Ile Val Val Ile Asp Glu Thr
            340                 345                 350 gct gct gtc ggc ttt aac ctc tct tta ggc att ggt ttc gaa gcg ggc        1104
Ala Ala Val Gly Phe Asn Leu Ser Leu Gly Ile Gly Phe Glu Ala Gly
        355                 360                 365 aac aag ccg aaa gaa ctg tac agc gaa gag gca gtc aac ggg gaa act        1152
Asn Lys Pro Lys Glu Leu Tyr Ser Glu Glu Ala Val Asn Gly Glu Thr
    370                 375                 380 cag caa gcg cac tta cag gcg att aaa gag ctg ata gcg cgt gac aaa        1200
Gln Gln Ala His Leu Gln Ala Ile Lys Glu Leu Ile Ala Arg Asp Lys
385                 390                 395                 400 aac cac cca agc gtg gtg atg tgg agt att gcc aac gaa ccg gat acc        1248
Asn His Pro Ser Val Val Met Trp Ser Ile Ala Asn Glu Pro Asp Thr
                405                 410                 415 cgt ccg caa ggt gca cgg gaa tat ttc gcg cca ctg gcg gaa gca acg        1296
Arg Pro Gln Gly Ala Arg Glu Tyr Phe Ala Pro Leu Ala Glu Ala Thr
            420                 425                 430 cgt aaa ctc gac ccg acg cgt ccg atc acc tgc gtc aat gta atg ttc        1344
Arg Lys Leu Asp Pro Thr Arg Pro Ile Thr Cys Val Asn Val Met Phe
        435                 440                 445 tgc gac gct cac acc gat acc atc agc gat ctc ttt gat gtg ctg tgc        1392
Cys Asp Ala His Thr Asp Thr Ile Ser Asp Leu Phe Asp Val Leu Cys
    450                 455                 460 ctg aac cgt tat tac gga tgg tat gtc caa agc ggc gat ttg gaa acg        1440
Leu Asn Arg Tyr Tyr Gly Trp Tyr Val Gln Ser Gly Asp Leu Glu Thr
465                 470                 475                 480 gca gag aag gta ctg gaa aaa gaa ctt ctg gcc tgg cag gag aaa ctg        1488
Ala Glu Lys Val Leu Glu Lys Glu Leu Leu Ala Trp Gln Glu Lys Leu
                485                 490                 495 cat cag ccg att atc atc acc gaa tac ggc gtg gat acg tta gcc ggg        1536
His Gln Pro Ile Ile Ile Thr Glu Tyr Gly Val Asp Thr Leu Ala Gly
            500                 505                 510 ctg cac tca atg tac acc gac atg tgg agt gaa gag tat cag tgt gca        1584
Leu His Ser Met Tyr Thr Asp Met Trp Ser Glu Glu Tyr Gln Cys Ala
        515                 520                 525 tgg ctg gat atg tat cac cgc gtc ttt gat cgc gtc agc gcc gtc gtc        1632
Trp Leu Asp Met Tyr His Arg Val Phe Asp Arg Val Ser Ala Val Val
    530                 535                 540 ggt gaa cag gta tgg aat ttc gcc gat ttt gcg acc tcg caa ggc ata        1680
Gly Glu Gln Val Trp Asn Phe Ala Asp Phe Ala Thr Ser Gln Gly Ile
545                 550                 555                 560 ttg cgc gtt ggc ggt aac aag aaa ggg atc ttc act cgc gac cgc aaa        1728
Leu Arg Val Gly Gly Asn Lys Lys Gly Ile Phe Thr Arg Asp Arg Lys
                565                 570                 575 ccg aag tcg gcg gct ttt ctg ctg caa aaa cgc tgg act ggc atg aac        1776
Pro Lys Ser Ala Ala Phe Leu Leu Gln Lys Arg Trp Thr Gly Met Asn
            580                 585                 590 ttc ggt gaa aaa ccg cag cag gga ggc aaa caa tga                        1812
Phe Gly Glu Lys Pro Gln Gln Gly Gly Lys Gln
        595                 600

<210> SEQ ID NO 30
<211> LENGTH: 603
<212> TYPE: PRT
<213> ORGANISM: Escherichia coli

<400> SEQUENCE: 30
```

```
Met Leu Arg Pro Val Glu Thr Pro Thr Arg Glu Ile Lys Lys Leu Asp
1               5                   10                  15
Gly Leu Trp Ala Phe Ser Leu Asp Arg Glu Asn Cys Gly Ile Asp Gln
                20                  25                  30
Arg Trp Trp Glu Ser Ala Leu Gln Glu Ser Arg Ala Ile Ala Val Pro
            35                  40                  45
Gly Ser Phe Asn Asp Gln Phe Ala Asp Ala Asp Ile Arg Asn Tyr Ala
        50                  55                  60
Gly Asn Val Trp Tyr Gln Arg Glu Val Phe Ile Pro Lys Gly Trp Ala
65                  70                  75                  80
Gly Gln Arg Ile Val Leu Arg Phe Asp Ala Val Thr His Tyr Gly Lys
                85                  90                  95
Val Trp Val Asn Asn Gln Glu Val Met Glu His Gln Gly Gly Tyr Thr
            100                 105                 110
Pro Phe Glu Ala Asp Val Thr Pro Tyr Val Ile Ala Gly Lys Ser Val
        115                 120                 125
Arg Ile Thr Val Cys Val Asn Asn Glu Leu Asn Trp Gln Thr Ile Pro
        130                 135                 140
Pro Gly Met Val Ile Thr Asp Glu Asn Gly Lys Lys Lys Gln Ser Tyr
145                 150                 155                 160
Phe His Asp Phe Phe Asn Tyr Ala Gly Ile His Arg Ser Val Met Leu
                165                 170                 175
Tyr Thr Thr Pro Asn Thr Trp Val Asp Asp Ile Thr Val Val Thr His
            180                 185                 190
Val Ala Gln Asp Cys Asn His Ala Ser Val Asp Trp Gln Val Val Ala
        195                 200                 205
Asn Gly Asp Val Ser Val Glu Leu Arg Asp Ala Asp Gln Gln Val Val
210                 215                 220
Ala Thr Gly Gln Gly Thr Ser Gly Thr Leu Gln Val Val Asn Pro His
225                 230                 235                 240
Leu Trp Gln Pro Gly Glu Gly Tyr Leu Tyr Glu Leu Cys Val Thr Ala
                245                 250                 255
Lys Ser Gln Thr Glu Cys Asp Ile Tyr Pro Leu Arg Val Gly Ile Arg
            260                 265                 270
Ser Val Ala Val Lys Gly Glu Gln Phe Leu Ile Asn His Lys Pro Phe
        275                 280                 285
Tyr Phe Thr Gly Phe Gly Arg His Glu Asp Ala Asp Leu Arg Gly Lys
        290                 295                 300
Gly Phe Asp Asn Val Leu Met Val His Asp His Ala Leu Met Asp Trp
305                 310                 315                 320
Ile Gly Ala Asn Ser Tyr Arg Thr Ser His Tyr Pro Tyr Ala Glu Glu
                325                 330                 335
Met Leu Asp Trp Ala Asp Glu His Gly Ile Val Val Ile Asp Glu Thr
            340                 345                 350
Ala Ala Val Gly Phe Asn Leu Ser Leu Gly Ile Gly Phe Glu Ala Gly
        355                 360                 365
Asn Lys Pro Lys Glu Leu Tyr Ser Glu Glu Ala Val Asn Gly Glu Thr
        370                 375                 380
Gln Gln Ala His Leu Gln Ala Ile Lys Glu Leu Ile Ala Arg Asp Lys
385                 390                 395                 400
Asn His Pro Ser Val Val Met Trp Ser Ile Ala Asn Glu Pro Asp Thr
                405                 410                 415
```

```
Arg Pro Gln Gly Ala Arg Glu Tyr Phe Ala Pro Leu Ala Glu Ala Thr
                420                 425                 430

Arg Lys Leu Asp Pro Thr Arg Pro Ile Thr Cys Val Asn Val Met Phe
            435                 440                 445

Cys Asp Ala His Thr Asp Thr Ile Ser Asp Leu Phe Asp Val Leu Cys
        450                 455                 460

Leu Asn Arg Tyr Tyr Gly Trp Tyr Val Gln Ser Gly Asp Leu Glu Thr
465                 470                 475                 480

Ala Glu Lys Val Leu Glu Lys Glu Leu Leu Ala Trp Gln Glu Lys Leu
                485                 490                 495

His Gln Pro Ile Ile Ile Thr Gly Tyr Gly Val Asp Thr Leu Ala Gly
            500                 505                 510

Leu His Ser Met Tyr Thr Asp Met Trp Ser Glu Glu Tyr Gln Cys Ala
        515                 520                 525

Trp Leu Asp Met Tyr His Arg Val Phe Asp Arg Val Ser Ala Val Val
530                 535                 540

Gly Glu Gln Val Trp Asn Phe Ala Asp Phe Ala Thr Ser Gln Gly Ile
545                 550                 555                 560

Leu Arg Val Gly Gly Asn Lys Lys Gly Ile Phe Thr Arg Asp Arg Lys
                565                 570                 575

Pro Lys Ser Ala Ala Phe Leu Leu Gln Lys Arg Trp Thr Gly Met Asn
            580                 585                 590

Phe Gly Glu Lys Pro Gln Gln Gly Gly Lys Gln
        595                 600

<210> SEQ ID NO 31
<211> LENGTH: 1812
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(1809)

<400> SEQUENCE: 31 atg ctc cgc ccc gtc gag acc ccc acc cgc gag atc aag aag ctc gac      48
Met Leu Arg Pro Val Glu Thr Pro Thr Arg Glu Ile Lys Lys Leu Asp
1               5                   10                  15 ggc ctc tgg gcc ttc tcg ctc gac cgc gag aac tgc ggc atc gac cag      96
Gly Leu Trp Ala Phe Ser Leu Asp Arg Glu Asn Cys Gly Ile Asp Gln
            20                  25                  30 cgt tgg tgg gag tcg gcc ctc cag gag tcg cgc gct atc gcc gtc ccc     144
Arg Trp Trp Glu Ser Ala Leu Gln Glu Ser Arg Ala Ile Ala Val Pro
        35                  40                  45 ggc tcg ttc aac gac cag ttc gcc gac gcc gac atc cgc aac tac gcc     192
Gly Ser Phe Asn Asp Gln Phe Ala Asp Ala Asp Ile Arg Asn Tyr Ala
    50                  55                  60 ggc aac gtc tgg tac cag cgc gag gtc ttt atc ccc aag ggc tgg gcc     240
Gly Asn Val Trp Tyr Gln Arg Glu Val Phe Ile Pro Lys Gly Trp Ala
65                  70                  75                  80 ggt cag cgc atc gtc ctc cgc ttc gac gcc gtc acc cac tac ggc aag     288
Gly Gln Arg Ile Val Leu Arg Phe Asp Ala Val Thr His Tyr Gly Lys
                85                  90                  95 gtc tgg gtc aac aac cag gag gtc atg gag cac cag ggc ggc tac acc     336
Val Trp Val Asn Asn Gln Glu Val Met Glu His Gln Gly Gly Tyr Thr
            100                 105                 110 ccc ttc gag gcc gac gtc acc ccc tac gtt atc gcc ggc aag tcg gtc     384
```

```
Pro Phe Glu Ala Asp Val Thr Pro Tyr Val Ile Ala Gly Lys Ser Val
        115                 120                 125 cgc atc acc gtc tgc gtc aac aac gag ttg aac tgg cag acc atc ccc    432
Arg Ile Thr Val Cys Val Asn Asn Glu Leu Asn Trp Gln Thr Ile Pro
130                 135                 140 cct ggc atg gtc atc acc gac gag aac ggc aag aag aag cag tcg tac    480
Pro Gly Met Val Ile Thr Asp Glu Asn Gly Lys Lys Lys Gln Ser Tyr
145                 150                 155                 160 ttc cac gac ttc ttc aac tac gct ggc atc cac cgc tcg gtc atg ctc    528
Phe His Asp Phe Phe Asn Tyr Ala Gly Ile His Arg Ser Val Met Leu
                165                 170                 175 tac acc acc ccc aac acc tgg gtc gac gac atc acc gtc gtc acc cac    576
Tyr Thr Thr Pro Asn Thr Trp Val Asp Asp Ile Thr Val Val Thr His
            180                 185                 190 gtc gcc cag gac tgc aac cac gcc tcg gtc gac tgg cag gtc gtc gcc    624
Val Ala Gln Asp Cys Asn His Ala Ser Val Asp Trp Gln Val Val Ala
        195                 200                 205 aac ggt gat gtt tcg gtc gag ttg cgc gac gct gac cag cag gtc gtt    672
Asn Gly Asp Val Ser Val Glu Leu Arg Asp Ala Asp Gln Gln Val Val
210                 215                 220 gcc acc ggc cag ggc acc tcg ggc acc ctc cag gtc gtc aac ccc cac    720
Ala Thr Gly Gln Gly Thr Ser Gly Thr Leu Gln Val Val Asn Pro His
225                 230                 235                 240 ctc tgg cag ccc ggc gag ggc tac ctc tac gag ttg tgc gtc acc gcc    768
Leu Trp Gln Pro Gly Glu Gly Tyr Leu Tyr Glu Leu Cys Val Thr Ala
                245                 250                 255 aag tcg cag acc gag tgc gac atc tac ccc ctc cgc gtc ggc atc cgc    816
Lys Ser Gln Thr Glu Cys Asp Ile Tyr Pro Leu Arg Val Gly Ile Arg
            260                 265                 270 tcg gtc gcc gtc aag ggc gag cag ttc ctc atc aac cac aag ccc ttc    864
Ser Val Ala Val Lys Gly Glu Gln Phe Leu Ile Asn His Lys Pro Phe
        275                 280                 285 tac ttc acc ggc ttc ggc cgc cac gag gac gct gat ctc cgc ggc aag    912
Tyr Phe Thr Gly Phe Gly Arg His Glu Asp Ala Asp Leu Arg Gly Lys
290                 295                 300 ggc ttc gac aac gtc ctc atg gtc cac gac cac gcc ctc atg gac tgg    960
Gly Phe Asp Asn Val Leu Met Val His Asp His Ala Leu Met Asp Trp
305                 310                 315                 320 atc ggc gcc aac tcg tac cgc acc tcg cac tac ccc tac gcc gag gag   1008
Ile Gly Ala Asn Ser Tyr Arg Thr Ser His Tyr Pro Tyr Ala Glu Glu
                325                 330                 335 atg ttg gac tgg gcc gac gag cac ggc atc gtc gtc atc gac gag acc   1056
Met Leu Asp Trp Ala Asp Glu His Gly Ile Val Val Ile Asp Glu Thr
            340                 345                 350 gcc gct gtc ggc ttc aac ctc tcg ctc ggc atc ggc ttc gag gcc ggc   1104
Ala Ala Val Gly Phe Asn Leu Ser Leu Gly Ile Gly Phe Glu Ala Gly
        355                 360                 365 aac aag ccc aag gag ttg tac tcg gag gag gcc gtc aac ggc gag acc   1152
Asn Lys Pro Lys Glu Leu Tyr Ser Glu Glu Ala Val Asn Gly Glu Thr
370                 375                 380 cag cag gcc cat ctc cag gcc atc aag gag ttg atc gcc cgc gac aag   1200
Gln Gln Ala His Leu Gln Ala Ile Lys Glu Leu Ile Ala Arg Asp Lys
385                 390                 395                 400 aac cac ccc tcc gtc gtc atg tgg tcg atc gcc aac gag ccc gac acc   1248
Asn His Pro Ser Val Val Met Trp Ser Ile Ala Asn Glu Pro Asp Thr
                405                 410                 415 cgt ccc cag ggt gcc cgc gag tac ttc gcc cct ctc gcc gag gcc acc   1296
Arg Pro Gln Gly Ala Arg Glu Tyr Phe Ala Pro Leu Ala Glu Ala Thr
            420                 425                 430
```

```
cgc aag ttg gac ccc acc cgc ccc att acc tgc gtc aac gtc atg ttc      1344
Arg Lys Leu Asp Pro Thr Arg Pro Ile Thr Cys Val Asn Val Met Phe
        435                 440                 445 tgc gac gcc cac acc gac acc atc tcg gac ctc ttc gac gtc ctc tgc      1392
Cys Asp Ala His Thr Asp Thr Ile Ser Asp Leu Phe Asp Val Leu Cys
450                 455                 460 ctc aac cgc tac tac ggc tgg tac gtc cag tcg ggc gac ctc gag act      1440
Leu Asn Arg Tyr Tyr Gly Trp Tyr Val Gln Ser Gly Asp Leu Glu Thr
465                 470                 475                 480 gcc gag aag gtc ctc gag aag gag ttg ctc gcc tgg cag gag aag ctc      1488
Ala Glu Lys Val Leu Glu Lys Glu Leu Leu Ala Trp Gln Glu Lys Leu
                485                 490                 495 cac cag ccc atc atc atc acc gag tac ggc gtc gac acc ctc gcc ggc      1536
His Gln Pro Ile Ile Ile Thr Glu Tyr Gly Val Asp Thr Leu Ala Gly
            500                 505                 510 ctc cac tcg atg tac acc gac atg tgg tcg gag gag tac cag tgc gcc      1584
Leu His Ser Met Tyr Thr Asp Met Trp Ser Glu Glu Tyr Gln Cys Ala
        515                 520                 525 tgg ctc gac atg tac cac cgc gtc ttt gac cgt gtc tcg gcc gtc gtc      1632
Trp Leu Asp Met Tyr His Arg Val Phe Asp Arg Val Ser Ala Val Val
530                 535                 540 ggc gag cag gtc tgg aac ttc gcc gac ttc gcc acc tcg cag ggc atc      1680
Gly Glu Gln Val Trp Asn Phe Ala Asp Phe Ala Thr Ser Gln Gly Ile
545                 550                 555                 560 ttg cgc gtc ggc ggc aac aag aag ggc atc ttc acc cgc gac cgc aag      1728
Leu Arg Val Gly Gly Asn Lys Lys Gly Ile Phe Thr Arg Asp Arg Lys
                565                 570                 575 ccc aag tcg gcc gcc ttc ttg ctc caa aag cgc tgg acc ggc atg aac      1776
Pro Lys Ser Ala Ala Phe Leu Leu Gln Lys Arg Trp Thr Gly Met Asn
            580                 585                 590 ttc ggt gag aag ccc cag cag ggc ggc aag cag taa                      1812
Phe Gly Glu Lys Pro Gln Gln Gly Gly Lys Gln
        595                 600

<210> SEQ ID NO 32
<211> LENGTH: 603
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 32

Met Leu Arg Pro Val Glu Thr Pro Thr Arg Glu Ile Lys Lys Leu Asp
1               5                   10                  15

Gly Leu Trp Ala Phe Ser Leu Asp Arg Glu Asn Cys Gly Ile Asp Gln
            20                  25                  30

Arg Trp Trp Glu Ser Ala Leu Gln Glu Ser Arg Ala Ile Ala Val Pro
        35                  40                  45

Gly Ser Phe Asn Asp Gln Phe Ala Asp Ala Asp Ile Arg Asn Tyr Ala
    50                  55                  60

Gly Asn Val Trp Tyr Gln Arg Glu Val Phe Ile Pro Lys Gly Trp Ala
65                  70                  75                  80

Gly Gln Arg Ile Val Leu Arg Phe Asp Ala Val Thr His Tyr Gly Lys
                85                  90                  95

Val Trp Val Asn Asn Gln Glu Val Met Glu His Gln Gly Gly Tyr Thr
            100                 105                 110

Pro Phe Glu Ala Asp Val Thr Pro Tyr Val Ile Ala Gly Lys Ser Val
        115                 120                 125
```

-continued

```
Arg Ile Thr Val Cys Val Asn Asn Glu Leu Asn Trp Gln Thr Ile Pro
        130                 135                 140

Pro Gly Met Val Ile Thr Asp Glu Asn Gly Lys Lys Gln Ser Tyr
145                 150                 155                 160

Phe His Asp Phe Phe Asn Tyr Ala Gly Ile His Arg Ser Val Met Leu
                165                 170                 175

Tyr Thr Thr Pro Asn Thr Trp Val Asp Ile Thr Val Val Thr His
                180                 185                 190

Val Ala Gln Asp Cys Asn His Ala Ser Val Asp Trp Gln Val Val Ala
            195                 200                 205

Asn Gly Asp Val Ser Val Glu Leu Arg Asp Ala Asp Gln Gln Val Val
210                 215                 220

Ala Thr Gly Gln Gly Thr Ser Gly Thr Leu Gln Val Val Asn Pro His
225                 230                 235                 240

Leu Trp Gln Pro Gly Glu Gly Tyr Leu Tyr Glu Leu Cys Val Thr Ala
                245                 250                 255

Lys Ser Gln Thr Glu Cys Asp Ile Tyr Pro Leu Arg Val Gly Ile Arg
            260                 265                 270

Ser Val Ala Val Lys Gly Glu Gln Phe Leu Ile Asn His Lys Pro Phe
    275                 280                 285

Tyr Phe Thr Gly Phe Gly Arg His Glu Asp Ala Asp Leu Arg Gly Lys
290                 295                 300

Gly Phe Asp Asn Val Leu Met Val His Asp His Ala Leu Met Asp Trp
305                 310                 315                 320

Ile Gly Ala Asn Ser Tyr Arg Thr Ser His Tyr Pro Tyr Ala Glu Glu
                325                 330                 335

Met Leu Asp Trp Ala Asp Glu His Gly Ile Val Val Ile Asp Glu Thr
            340                 345                 350

Ala Ala Val Gly Phe Asn Leu Ser Leu Gly Ile Gly Phe Glu Ala Gly
            355                 360                 365

Asn Lys Pro Lys Glu Leu Tyr Ser Glu Glu Ala Val Asn Gly Glu Thr
370                 375                 380

Gln Gln Ala His Leu Gln Ala Ile Lys Glu Leu Ile Ala Arg Asp Lys
385                 390                 395                 400

Asn His Pro Ser Val Val Met Trp Ser Ile Ala Asn Glu Pro Asp Thr
                405                 410                 415

Arg Pro Gln Gly Ala Arg Glu Tyr Phe Ala Pro Leu Ala Glu Ala Thr
            420                 425                 430

Arg Lys Leu Asp Pro Thr Arg Pro Ile Thr Cys Val Asn Val Met Phe
    435                 440                 445

Cys Asp Ala His Thr Asp Thr Ile Ser Asp Leu Phe Asp Val Leu Cys
450                 455                 460

Leu Asn Arg Tyr Tyr Gly Trp Tyr Val Gln Ser Gly Asp Leu Glu Thr
465                 470                 475                 480

Ala Glu Lys Val Leu Glu Lys Glu Leu Leu Ala Trp Gln Glu Lys Leu
                485                 490                 495

His Gln Pro Ile Ile Ile Thr Glu Tyr Gly Val Asp Thr Leu Ala Gly
            500                 505                 510

Leu His Ser Met Tyr Thr Asp Met Trp Ser Glu Glu Tyr Gln Cys Ala
            515                 520                 525

Trp Leu Asp Met Tyr His Arg Val Phe Asp Arg Val Ser Ala Val Val
530                 535                 540

Gly Glu Gln Val Trp Asn Phe Ala Asp Phe Ala Thr Ser Gln Gly Ile
```

```
            545                 550                 555                 560
Leu Arg Val Gly Gly Asn Lys Lys Gly Ile Phe Thr Arg Asp Arg Lys
                        565                 570                 575

Pro Lys Ser Ala Ala Phe Leu Leu Gln Lys Arg Trp Thr Gly Met Asn
                580                 585                 590

Phe Gly Glu Lys Pro Gln Gln Gly Gly Lys Gln
                595                 600
```

<210> SEQ ID NO 33
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 33
aatatctaga tgaccgtgcg cttttttgaga c          31

<210> SEQ ID NO 34
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 34
agcaactagt cgtatatttg ttgaaaggtg           30

<210> SEQ ID NO 35
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 35
attttctaga cacctcaaaa acgtgccttg           30

<210> SEQ ID NO 36
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 36
aataactagt ggcggatatg tgtatggag            29

<210> SEQ ID NO 37
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 37
aacgtctaga cgtgttatct tgcgctgc             28

<210> SEQ ID NO 38
<211> LENGTH: 29

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 38
tcatactagt gatgatttag aggtgttgg                                    29

<210> SEQ ID NO 39
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 39
aagctctaga gactgtaaag acggaggggg                                   29

<210> SEQ ID NO 40
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 40
agtaactagt tgtggatagt gggtagtgg                                    29

<210> SEQ ID NO 41
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 41
aaagtctaga ctggcaatag ttagtgcacg                                   30

<210> SEQ ID NO 42
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 42
atcaactagt gatggaggtt tgtttgagaa g                                 31

<210> SEQ ID NO 43
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 43
atcatctaga gagctcaaga tgaaggtgct c                                 31

<210> SEQ ID NO 44
<211> LENGTH: 29
<212> TYPE: DNA
```

```
<213> ORGANISM: Artificial Sequence
<220> FEATURE:
<223> OTHER INFORMATION: Description of Artificial Sequence: Synthetic
      primer

<400> SEQUENCE: 44
aataactagt ggtgtgtgtg gtttgcggg                                    29

<210> SEQ ID NO 45
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 45
ttagtctaga aaagtgctgc ttcggaacc                                    29

<210> SEQ ID NO 46
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 46
agatactagt gatgtagatg tgagtgtgag                                   30

<210> SEQ ID NO 47
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 47
aatatctaga ggttccgaga ggtggatttg                                   30

<210> SEQ ID NO 48
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 48
ataatctaga tggctcctga aaggacgag                                    29

<210> SEQ ID NO 49
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 49
agcatctaga aaaactattc aataatgggc g                                 31

<210> SEQ ID NO 50
<211> LENGTH: 30
<212> TYPE: DNA
<213> ORGANISM: Artificial Sequence
```

```
<220> FEATURE:
<223> OTHER INFORMATION: Description of Artificial Sequence: Synthetic
      primer

<400> SEQUENCE: 50
atttctagaa tggcgagacg caggggtag                                    30

<210> SEQ ID NO 51
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 51
aatatctaga gagtgggcac tgaactaaaa ag                                32

<210> SEQ ID NO 52
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 52
aatatctaga gacactgcat gacgcgaaat c                                 31

<210> SEQ ID NO 53
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 53
aagtctagat gtcaatcatc tttgctgctg                                   30

<210> SEQ ID NO 54
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 54
tgcgtctaga attataatta taatgaggaa gtg                               33

<210> SEQ ID NO 55
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 55
ttatctagag gcgagtggcg gactgc                                       26

<210> SEQ ID NO 56
<211> LENGTH: 29
<212> TYPE: DNA
<213> ORGANISM: Artificial Sequence
<220> FEATURE:
```

<223> OTHER INFORMATION: Description of Artificial Sequence: Synthetic
      primer

<400> SEQUENCE: 56
ttgtctagac aattggcaag gctgggttg                                           29

<210> SEQ ID NO 57
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 57
aatatctaga gatcctggtc gaaaaagaca g                                        31

<210> SEQ ID NO 58
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 58
aatgtctaga tgagtttctg ttttttcctt tttgc                                    35

<210> SEQ ID NO 59
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 59
aatatctaga tgaacaattc atgcagcttc acg                                      33

<210> SEQ ID NO 60
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 60
aatatctaga cgtctaagcg tttacgtgcc                                          30

<210> SEQ ID NO 61
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 61
aatatctaga ctcgttttga tggagttctc                                          30

<210> SEQ ID NO 62
<211> LENGTH: 31
<212> TYPE: DNA
<213> ORGANISM: Artificial Sequence
<220> FEATURE:
<223> OTHER INFORMATION: Description of Artificial Sequence: Synthetic -continued

```
      primer

<400> SEQUENCE: 62
atttctagat gcatttacag gtgaatatta c                                 31

<210> SEQ ID NO 63
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 63
ttatctagac ataaaagtgt ctggagcg                                     28

<210> SEQ ID NO 64
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 64
ttatctagaa ctaagtggtg tctactttgg                                   30

<210> SEQ ID NO 65
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 65
aattctagag gatactccat ccccaccc                                     28

<210> SEQ ID NO 66
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 66
aattctagac agttaccgtg cgcccactg                                    29

<210> SEQ ID NO 67
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 67
aattctagac tttcacaaat aggcatccta tc                                32

<210> SEQ ID NO 68
<211> LENGTH: 31
<212> TYPE: DNA
<213> ORGANISM: Artificial Sequence
<220> FEATURE:
<223> OTHER INFORMATION: Description of Artificial Sequence: Synthetic
      primer
```

-continued

```
<400> SEQUENCE: 68
aattctagag gcttttcgt ttattggatt g                                    31

<210> SEQ ID NO 69
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 69
acgtctagat atccaattct caccacttc                                      29

<210> SEQ ID NO 70
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 70
aattctagat tttactaccg cattcccttt tc                                  32

<210> SEQ ID NO 71
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 71
acgtctagac cttttcagta aacaatttc                                      29

<210> SEQ ID NO 72
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 72
atttctagac acaaagaaga agggtgtgtc                                     30

<210> SEQ ID NO 73
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 73
acgtctagaa ctgttttctt gaaacttc                                       28

<210> SEQ ID NO 74
<211> LENGTH: 30
<212> TYPE: DNA
<213> ORGANISM: Artificial Sequence
<220> FEATURE:
<223> OTHER INFORMATION: Description of Artificial Sequence: Synthetic
      primer
```

<400> SEQUENCE: 74
agtaactagt tgacggcgtg tatatgtcag                                    30

<210> SEQ ID NO 75
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 75
aggtactagt ccattgtatc gatttctgat                                    30

<210> SEQ ID NO 76
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 76
agtaactagt gctatgcgaa cggttcattt tg                                 32

<210> SEQ ID NO 77
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 77
aggtactagt tttttctctct ctggtgtgaa cg                                32

<210> SEQ ID NO 78
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 78
aattctagac gcagagtgat ggtcattacc                                    30

<210> SEQ ID NO 79
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 79
aattctagac tctatggcaa gattacgag                                     29

<210> SEQ ID NO 80
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 80

```
aattctagat gctcgtgaag aggggcac                                               28

<210> SEQ ID NO 81
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 81
acgtctagac atttttttgcc gccaattctg                                            30

<210> SEQ ID NO 82
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 82
atttctagac ccccgcctat ttttttttc                                              30
```